United States Patent
Mondon et al.

(10) Patent No.: US 12,247,076 B2
(45) Date of Patent: Mar. 11, 2025

(54) USE OF MODIFIED Fc FRAGMENTS IN IMMUNOTHERAPY

(71) Applicant: Laboratoire Français du Fractionnement et des Biotechnologies, Les Ulis (FR)

(72) Inventors: Philippe Mondon, Neuve Chapelle (FR); Céline Monnet-Mars, Lambersart (FR); Alexandre Fontayne, La Madeleine (FR); Christophe De Romeuf, Lambersart (FR); Abdessatar Chtourou, Elancourt (FR)

(73) Assignee: Laboratoire Français du Fractionnement et des Biotechnologies, Les Ulis (FR)

( * ) Notice: Subject to any disclaimer, the term of this patent is extended or adjusted under 35 U.S.C. 154(b) by 16 days.

(21) Appl. No.: 15/742,268

(22) PCT Filed: Jul. 6, 2016

(86) PCT No.: PCT/FR2016/051708
§ 371 (c)(1),
(2) Date: Jan. 5, 2018

(87) PCT Pub. No.: WO2017/006052
PCT Pub. Date: Jan. 12, 2017

(65) Prior Publication Data
US 2018/0355034 A1  Dec. 13, 2018

(30) Foreign Application Priority Data

Jul. 6, 2015  (FR) ..................... 1556399

(51) Int. Cl.
| | | |
|---|---|---|
| A61K 39/395 | (2006.01) | |
| A61K 39/00 | (2006.01) | |
| A61P 37/06 | (2006.01) | |
| C07K 16/00 | (2006.01) | |
| C07K 16/28 | (2006.01) | |

(52) U.S. Cl.
CPC ........ *C07K 16/283* (2013.01); *A61K 39/0008* (2013.01); *A61K 39/001* (2013.01); *A61P 37/06* (2018.01); *C07K 16/00* (2013.01); *A61K 2039/55* (2013.01); *C07K 2317/52* (2013.01); *C07K 2317/70* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,784,950 A | 11/1988 | Hagen et al. |
| 4,816,397 A | 3/1989 | Boss et al. |
| 4,816,567 A | 3/1989 | Cabilly et al. |
| 4,873,316 A | 10/1989 | Meade et al. |
| 4,946,778 A | 8/1990 | Ladner et al. |
| 5,202,238 A | 4/1993 | Fell et al. |
| 5,304,489 A | 4/1994 | Rosen |
| 5,322,775 A | 6/1994 | Clark et al. |
| 5,545,806 A | 8/1996 | Lonberg et al. |
| 5,545,807 A | 8/1996 | Surani et al. |
| 5,576,040 A | 11/1996 | Moller et al. |
| 5,589,604 A | 12/1996 | Drohan et al. |
| 5,591,669 A | 1/1997 | Krimpenfort et al. |
| 5,633,076 A | 5/1997 | DeBoer et al. |
| 5,639,940 A | 6/1997 | Garner et al. |
| 5,648,243 A | 7/1997 | Hurwitz et al. |
| 5,648,253 A | 7/1997 | Wei |
| 5,741,957 A | 4/1998 | Doboer et al. |
| 5,750,172 A | 5/1998 | Meade et al. |
| 5,756,687 A | 5/1998 | Denman et al. |
| 5,780,009 A | 7/1998 | Karatzas et al. |
| 5,827,690 A | 10/1998 | Meade et al. |
| 5,831,141 A | 11/1998 | Lubon et al. |
| 5,843,705 A | 12/1998 | DiTullio et al. |
| 5,849,992 A | 12/1998 | Meade et al. |
| 5,892,070 A | 4/1999 | Prieto et al. |
| 5,945,577 A | 8/1999 | Stice et al. |
| 5,965,789 A | 10/1999 | Lubon et al. |
| 6,013,857 A | 1/2000 | Deboer et al. |
| 6,063,905 A | 5/2000 | Capra et al. |
| 6,140,552 A | 10/2000 | Deboer et al. |
| 6,150,584 A | 11/2000 | Kucherlapati et al. |
| 6,201,167 B1 | 3/2001 | Pothier |

(Continued)

FOREIGN PATENT DOCUMENTS

| | | |
|---|---|---|
| CA | 2 634 997 A1 | 12/2007 |
| CN | 1273602 A | 11/2000 |

(Continued)

OTHER PUBLICATIONS

Howard et al. Neurology, 2019, 92;23:e2662-e2673, p. e2662. (Year: 2019).*

(Continued)

*Primary Examiner* — Chun W Dahle
(74) *Attorney, Agent, or Firm* — Wolf, Greenfield & Sacks, P.C.

(57) ABSTRACT

The present invention relates to the use of antibody Fc fragments in the treatment of autoimmune and/or inflammatory diseases, said Fc fragments being isolated recombinant Fc fragments having a modified affinity for at least one of the Fc receptors (FcR), particularly an increased affinity to FcRn.

8 Claims, 5 Drawing Sheets

Specification includes a Sequence Listing.

(56) References Cited

U.S. PATENT DOCUMENTS

| | | |
|---|---|---|
| 6,204,431 B1 | 3/2001 | Prieto et al. |
| 6,210,736 B1 | 4/2001 | Echelard et al. |
| 6,217,866 B1 | 4/2001 | Schlessinger et al. |
| 6,268,487 B1 | 7/2001 | Kutzko et al. |
| 6,271,436 B1 | 8/2001 | Piedrahita et al. |
| 6,441,145 B1 | 8/2002 | DiTullio et al. |
| 6,448,469 B1 | 9/2002 | Smith |
| 6,472,584 B1 | 10/2002 | Smith |
| 6,528,699 B1 | 3/2003 | Meade et al. |
| 6,545,198 B1 | 4/2003 | Echelard et al. |
| 6,548,653 B1 | 4/2003 | Young et al. |
| 6,580,017 B1 | 6/2003 | Echelard et al. |
| 6,593,463 B1 | 7/2003 | Chen et al. |
| 6,727,405 B1 | 4/2004 | Gordon et al. |
| 6,743,966 B2 | 6/2004 | Smith |
| 6,924,412 B1 | 8/2005 | de Groot et al. |
| 6,933,368 B2 | 8/2005 | Co et al. |
| 7,019,193 B2 | 3/2006 | Ditullio et al. |
| 7,029,872 B2 | 4/2006 | Gerngross |
| 7,045,676 B1 | 5/2006 | Gordon et al. |
| 7,053,202 B2 | 5/2006 | O'Keefe et al. |
| 7,087,719 B2 | 8/2006 | Visuri et al. |
| 7,101,971 B2 | 9/2006 | Meade et al. |
| 7,354,594 B2 | 4/2008 | Chen et al. |
| 7,501,553 B2 | 3/2009 | Chen et al. |
| 7,531,632 B2 | 5/2009 | Perreault |
| 7,550,263 B2 | 6/2009 | Meade et al. |
| 7,579,170 B2 * | 8/2009 | Beliard ............... A61P 7/04 435/70.21 |
| 7,632,980 B1 | 12/2009 | Chen et al. |
| 7,651,686 B2 | 1/2010 | Chen et al. |
| 7,662,925 B2 * | 2/2010 | Lazar ............... C07K 16/00 530/387.1 |
| 7,700,321 B2 | 4/2010 | McPherson et al. |
| 7,867,491 B2 | 1/2011 | Yang et al. |
| 7,928,064 B2 | 4/2011 | DiTullio et al. |
| 7,931,895 B2 | 4/2011 | Beliard et al. |
| 7,939,317 B1 | 5/2011 | Gordon et al. |
| 8,067,232 B2 * | 11/2011 | Kanda ............... C12N 9/90 435/325 |
| 8,173,860 B2 | 5/2012 | Meade et al. |
| 9,511,087 B2 | 12/2016 | Frieling et al. |
| 10,034,921 B2 | 7/2018 | Chen et al. |
| 10,174,110 B2 | 1/2019 | Meade et al. |
| 10,611,826 B2 | 4/2020 | Paolantonacci et al. |
| 2002/0131957 A1 | 9/2002 | Gavin et al. |
| 2002/0144299 A1 | 10/2002 | Chen et al. |
| 2002/0155998 A1 | 10/2002 | Young et al. |
| 2003/0005468 A1 | 1/2003 | Meade et al. |
| 2003/0033618 A1 | 2/2003 | Smith |
| 2003/0036637 A1 | 2/2003 | Fulton |
| 2003/0046716 A1 | 3/2003 | Echelard et al. |
| 2003/0096974 A1 | 5/2003 | Ditullio et al. |
| 2003/0140358 A1 | 7/2003 | Nuijens et al. |
| 2003/0175884 A1 | 9/2003 | Umana et al. |
| 2003/0177513 A1 | 9/2003 | Echelard et al. |
| 2003/0204860 A1 | 10/2003 | Melican et al. |
| 2003/0213003 A1 | 11/2003 | Meade et al. |
| 2004/0006776 A1 | 1/2004 | Meade et al. |
| 2004/0025193 A1 | 2/2004 | Echelard et al. |
| 2004/0033561 A1 | 2/2004 | O'Keefe et al. |
| 2004/0068760 A1 | 4/2004 | Robl et al. |
| 2004/0092719 A1 | 5/2004 | Birck-Wilson et al. |
| 2004/0097710 A1 | 5/2004 | Visuri et al. |
| 2004/0098755 A1 | 5/2004 | Mulroy et al. |
| 2004/0102380 A1 | 5/2004 | Fulton et al. |
| 2004/0109847 A1 | 6/2004 | Chen et al. |
| 2004/0117863 A1 | 6/2004 | Edge et al. |
| 2004/0121303 A1 | 6/2004 | Gavin et al. |
| 2004/0132101 A1 | 7/2004 | Lazar et al. |
| 2004/0133931 A1 | 7/2004 | Gavin et al. |
| 2004/0143857 A1 | 7/2004 | Young et al. |
| 2004/0148648 A1 | 7/2004 | Behboodi et al. |
| 2004/0167320 A1 | 8/2004 | Couto et al. |
| 2004/0192595 A1 | 9/2004 | Murakami et al. |
| 2004/0205832 A1 | 10/2004 | Meade et al. |
| 2004/0226052 A1 | 11/2004 | Meade et al. |
| 2004/0226053 A1 | 11/2004 | Meade et al. |
| 2005/0006307 A1 | 1/2005 | Jones et al. |
| 2005/0013811 A1 | 1/2005 | Chen et al. |
| 2005/0037000 A1 | 2/2005 | Stavenhagen et al. |
| 2005/0060766 A1 | 3/2005 | Chen |
| 2005/0071890 A1 | 3/2005 | Chen et al. |
| 2005/0097625 A1 | 5/2005 | Meade et al. |
| 2005/0123546 A1 | 6/2005 | Umana et al. |
| 2005/0158832 A1 | 7/2005 | Young et al. |
| 2005/0160483 A1 | 7/2005 | Meade et al. |
| 2005/0169908 A1 | 8/2005 | Murakami et al. |
| 2005/0177882 A1 | 8/2005 | Gavin et al. |
| 2005/0181482 A1 | 8/2005 | Meade et al. |
| 2005/0186608 A1 | 8/2005 | Olsen |
| 2005/0192226 A1 | 9/2005 | Enkhbaatar et al. |
| 2005/0193431 A1 | 9/2005 | Echelard et al. |
| 2005/0197496 A1 | 9/2005 | Perreault |
| 2005/0208000 A1 | 9/2005 | Bernstein et al. |
| 2005/0229261 A1 | 10/2005 | Cheng et al. |
| 2005/0235371 A1 | 10/2005 | Chen et al. |
| 2005/0245444 A1 | 11/2005 | Echelard et al. |
| 2005/0260672 A1 | 11/2005 | Couto et al. |
| 2006/0026695 A1 | 2/2006 | Edge et al. |
| 2006/0057638 A1 | 3/2006 | Bosques et al. |
| 2006/0105347 A1 | 5/2006 | Meade et al. |
| 2006/0121004 A1 | 6/2006 | Echelard et al. |
| 2006/0123500 A1 | 6/2006 | Echelard et al. |
| 2006/0127950 A1 | 6/2006 | Bosques et al. |
| 2006/0130159 A1 | 6/2006 | Masiello et al. |
| 2006/0168671 A1 | 7/2006 | Gavin et al. |
| 2006/0174359 A1 | 8/2006 | Melican et al. |
| 2006/0178309 A1 | 8/2006 | Visuri et al. |
| 2006/0179493 A1 | 8/2006 | Meade et al. |
| 2006/0179500 A1 | 8/2006 | Meade et al. |
| 2006/0182744 A1 | 8/2006 | Strome et al. |
| 2006/0188439 A1 | 8/2006 | Strome et al. |
| 2006/0191025 A1 | 8/2006 | Echelard et al. |
| 2006/0191029 A1 | 8/2006 | Gavin et al. |
| 2006/0253913 A1 | 11/2006 | Huang et al. |
| 2006/0272036 A1 | 11/2006 | Hammarstrom et al. |
| 2006/0286548 A1 | 12/2006 | Liposky et al. |
| 2007/0015239 A1 | 1/2007 | Bihoreau et al. |
| 2007/0037192 A1 | 2/2007 | Ziomek et al. |
| 2007/0048300 A1 | 3/2007 | Taylor et al. |
| 2007/0065912 A1 | 3/2007 | Carson et al. |
| 2007/0092521 A1 | 4/2007 | McPherson et al. |
| 2007/0192878 A1 | 8/2007 | Perreault |
| 2008/0004212 A1 | 1/2008 | Echelard et al. |
| 2008/0019905 A9 | 1/2008 | Strome et al. |
| 2008/0063780 A1 | 3/2008 | Meade et al. |
| 2008/0118501 A1 | 5/2008 | Schindler et al. |
| 2008/0176786 A1 | 7/2008 | Ditullio et al. |
| 2009/0068193 A1 | 3/2009 | Chen et al. |
| 2009/0178147 A1 | 7/2009 | Harvey |
| 2009/0239788 A1 | 9/2009 | Chtourou et al. |
| 2009/0246194 A1 | 10/2009 | Meade et al. |
| 2009/0252724 A1 | 10/2009 | Loetscher et al. |
| 2010/0021612 A1 | 1/2010 | Meade et al. |
| 2010/0056757 A1 | 3/2010 | Perreault |
| 2010/0081794 A1 | 4/2010 | Liu et al. |
| 2010/0143370 A1 | 6/2010 | De Romeuf et al. |
| 2010/0173323 A1 | 7/2010 | Strome et al. |
| 2010/0178292 A1 | 7/2010 | Wang et al. |
| 2010/0266611 A1 | 10/2010 | Chen et al. |
| 2011/0070167 A1 | 3/2011 | Enkhbaatar et al. |
| 2011/0082083 A1 | 4/2011 | Magneson et al. |
| 2011/0104049 A1 | 5/2011 | Strome et al. |
| 2011/0229460 A1 | 9/2011 | Meade et al. |
| 2012/0009188 A1 * | 1/2012 | Behrens ............... A61P 11/06 424/133.1 |
| 2012/0020984 A1 | 1/2012 | Lenz et al. |
| 2012/0058047 A9 | 3/2012 | Strome et al. |
| 2012/0301919 A1 | 11/2012 | Yang et al. |
| 2013/0149301 A1 | 6/2013 | Meade |
| 2013/0324619 A1 | 12/2013 | Chtourou |
| 2014/0046033 A1 | 2/2014 | Schindler et al. |
| 2014/0194360 A1 | 7/2014 | Frieling et al. |

(56) References Cited

U.S. PATENT DOCUMENTS

| | | | |
|---|---|---|---|
| 2014/0206617 A1 | 7/2014 | Frieling et al. | |
| 2014/0228301 A1 | 8/2014 | Meade et al. | |
| 2014/0242182 A1 | 8/2014 | Evans et al. | |
| 2014/0296490 A1 | 10/2014 | Faid et al. | |
| 2015/0175678 A1 | 6/2015 | Cavacini et al. | |
| 2015/0218239 A1* | 8/2015 | Ulrichts | A61P 19/00 424/133.1 |
| 2015/0368334 A1 | 12/2015 | Meade et al. | |
| 2015/0368357 A1 | 12/2015 | Meade et al. | |
| 2015/0374801 A1 | 12/2015 | Chen et al. | |
| 2016/0002330 A1 | 1/2016 | Meade | |
| 2016/0039913 A1 | 2/2016 | Meade et al. | |
| 2016/0089422 A1 | 3/2016 | Chtourou et al. | |
| 2016/0129115 A1 | 5/2016 | Magneson et al. | |
| 2016/0158676 A1 | 6/2016 | Hawkins et al. | |
| 2016/0168229 A1 | 6/2016 | Paolantonacci et al. | |
| 2016/0326547 A1 | 11/2016 | Meade et al. | |
| 2017/0121402 A1 | 5/2017 | Chtourou | |
| 2017/0129966 A1 | 5/2017 | Masiello | |
| 2017/0190753 A1 | 7/2017 | Abache | |
| 2018/0030111 A1* | 2/2018 | Monnet | G01N 33/53 |
| 2018/0139938 A1 | 5/2018 | Chen | |
| 2018/0169297 A1 | 6/2018 | Chtourou et al. | |
| 2018/0355034 A1 | 12/2018 | Mondon et al. | |
| 2019/0254276 A1 | 8/2019 | Chtourou | |
| 2019/0309057 A1 | 10/2019 | Meade et al. | |
| 2019/0309058 A1 | 10/2019 | Meade et al. | |
| 2020/0255518 A1 | 8/2020 | Schindler et al. | |
| 2020/0331994 A1 | 10/2020 | Chtourou et al. | |
| 2021/0275668 A1 | 9/2021 | Plantier et al. | |

FOREIGN PATENT DOCUMENTS

| | | |
|---|---|---|
| CN | 1387399 A | 12/2002 |
| CN | 1607960 A | 4/2005 |
| CN | 101213211 A | 7/2008 |
| CN | 101460522 A | 6/2009 |
| CN | 101484470 A | 7/2009 |
| CN | 101506238 A | 8/2009 |
| CN | 101588817 A | 11/2009 |
| CN | 101646775 A | 2/2010 |
| CN | 101802210 A | 8/2010 |
| CN | 102292640 A | 12/2011 |
| CN | 107454906 A | 12/2017 |
| DE | 40 00 939 A1 | 7/1991 |
| EP | 0 200 421 A2 | 11/1986 |
| EP | 0 279 582 A2 | 8/1988 |
| EP | 475354 A2 | 3/1992 |
| EP | 0 527 063 A1 | 2/1993 |
| EP | 0 791 652 A1 | 8/1997 |
| EP | 1 400 171 A1 | 3/2004 |
| EP | 1 688 488 A1 | 8/2006 |
| EP | 1 985 633 A1 | 10/2008 |
| EP | 2 233 500 A1 | 9/2010 |
| EP | 2 292 273 A2 | 3/2011 |
| EP | 1 945 665 B1 | 12/2011 |
| EP | 2 687 595 A1 | 1/2014 |
| EP | 3283099 B1 | 2/2018 |
| EP | 2 956 484 B1 | 11/2018 |
| FR | 2 861 080 A1 | 4/2005 |
| JP | H9-506779 A | 7/1997 |
| JP | 2000-507810 A | 6/2000 |
| JP | 2002-512014 A | 4/2002 |
| JP | 2003-521915 A | 7/2003 |
| JP | 2003-534781 A | 11/2003 |
| JP | 2006-507839 A | 3/2006 |
| JP | 2006-524039 A | 10/2006 |
| JP | 2007-533299 A | 11/2007 |
| JP | 2008-515772 A | 5/2008 |
| JP | 2008-543868 A | 12/2008 |
| JP | 2009-507482 A | 2/2009 |
| JP | 2009-508470 A | 3/2009 |
| JP | 2009-512694 A | 3/2009 |
| JP | 2009-521520 A | 6/2009 |
| JP | 2009-532477 A | 9/2009 |
| JP | 2009-538885 A | 11/2009 |
| JP | 2010-502204 A | 1/2010 |
| WO | WO 88/01648 A1 | 3/1988 |
| WO | WO 90/04036 A1 | 4/1990 |
| WO | WO 90/05188 A1 | 5/1990 |
| WO | WO 91/08216 A1 | 6/1991 |
| WO | WO 92/03918 A1 | 3/1992 |
| WO | WO 93/12227 A1 | 6/1993 |
| WO | WO 95/17085 A1 | 6/1995 |
| WO | WO 95/24488 A1 | 9/1995 |
| WO | WO 95/24494 A1 | 9/1995 |
| WO | WO 95/24495 A1 | 9/1995 |
| WO | WO 97/05771 A2 | 2/1997 |
| WO | WO 97/07669 A1 | 3/1997 |
| WO | WO 98/13378 A1 | 4/1998 |
| WO | WO 99/11773 A1 | 3/1999 |
| WO | WO 99/54342 A1 | 10/1999 |
| WO | WO 00/30436 A1 | 6/2000 |
| WO | WO 01/00855 A1 | 1/2001 |
| WO | WO 01/26455 A1 | 4/2001 |
| WO | WO 01/057088 A1 | 8/2001 |
| WO | WO 01/77181 A2 | 10/2001 |
| WO | WO 02/30954 A1 | 4/2002 |
| WO | WO 02/072636 A2 | 9/2002 |
| WO | WO 03/035835 A2 | 5/2003 |
| WO | WO 2004/040221 A1 | 5/2004 |
| WO | WO 2004/048517 A2 | 6/2004 |
| WO | WO 2004/050847 A2 | 6/2004 |
| WO | WO 2005/035753 A1 | 4/2005 |
| WO | WO 2006/014683 A2 | 2/2006 |
| WO | WO 2006/041656 A2 | 4/2006 |
| WO | WO 2006/088447 A1 | 8/2006 |
| WO | WO 2006/088464 A2 | 8/2006 |
| WO | WO 2006/109592 A1 | 10/2006 |
| WO | WO 2006/138553 A2 | 12/2006 |
| WO | WO 2006/138737 A2 | 12/2006 |
| WO | WO 2007/005786 A2 | 1/2007 |
| WO | WO 2007/014162 A2 | 2/2007 |
| WO | WO 2007/029054 A1 | 3/2007 |
| WO | WO 2007/048077 A2 | 4/2007 |
| WO | WO 2007/048122 A2 | 4/2007 |
| WO | WO 2007/115813 A1 | 10/2007 |
| WO | WO 2007/117505 A2 | 10/2007 |
| WO | WO 2007/149567 A2 | 12/2007 |
| WO | WO 2008/028686 A2 | 3/2008 |
| WO | WO 2008/063982 A2 | 5/2008 |
| WO | WO 2008/083150 A2 | 7/2008 |
| WO | WO 2008/101177 A2 | 8/2008 |
| WO | WO 2009/046168 A1 | 4/2009 |
| WO | WO 2010/127939 A1 | 11/2010 |
| WO | WO 2010/149907 A1 | 12/2010 |
| WO | WO 2011/060069 A3 | 5/2011 |
| WO | WO 2011/077102 A1 | 6/2011 |
| WO | WO 2012/067176 A1 | 5/2012 |
| WO | WO 2012/105699 A1 | 8/2012 |
| WO | WO 2013/021279 A2 | 2/2013 |
| WO | WO 2013/046704 A2 | 4/2013 |
| WO | WO 2013/095966 A1 | 6/2013 |
| WO | WO 2013/106577 A2 | 7/2013 |
| WO | WO 2013/163630 A1 | 10/2013 |
| WO | WO 2014/125374 A2 | 8/2014 |
| WO | WO 2014/125377 A2 | 8/2014 |
| WO | WO 2014/140927 A2 | 9/2014 |
| WO | WO 2014/151910 A1 | 9/2014 |
| WO | WO 2015/186004 A2 | 12/2015 |
| WO | WO 2016/166014 A1 | 10/2016 |
| WO | WO 2017/145166 A1 | 8/2017 |
| WO | WO 2017/188356 A1 | 11/2017 |
| WO | WO 2018/047813 A1 | 3/2018 |
| WO | WO 2018/098363 A2 | 5/2018 |

OTHER PUBLICATIONS

Psaila et al. The Journal of Clinical Investigation 2008, 118;8:2677-2681. (Year: 2008).*

[No Author Listed] GTC Biotherapeutics and LFB Biotechnologies Enter Strategic Collaboration for Recombinant Plasma Proteins and

(56) References Cited

OTHER PUBLICATIONS

Monoclonal Antibodies. Press Release; Oct. 2, 2006. Last accessed from <https://www.businesswire.com/news/home/20061002005515/en/GTC-Biotherapeutics-LFB-Biotechnologies-Enter-Strategic-Collaboration> on Jan. 19, 2018.
[No Author Listed] Herceptin® Trastuzumab. Genentech, Inc.; US Package Insert. Sep. 1998.
[No Author Listed] Trastuzumab. Wikipedia. Oct. 30, 2012.
Alzari, P.M. et al., Three-Dimensional Structure of Antibodies. Ann. Rev. Immunol. 1988 6: 555-580.
Anolik et al., The relationship of FcgammaRIIIa genotype to degree of B cell depletion by rituximab in the treatment of systemic lupus erythematosus. Arthritis Rheum. Feb. 2003;48(2):455-9.
Anthony et al., Identification of a receptor required for the anti-inflammatory activity of IVIG. Proc Natl Acad Sci U S A. Dec. 16, 2008;105(50):19571-8. doi: 10.1073/pnas.0810163105. Epub Nov. 26, 2008.
Awwad et al., Modification of monoclonal antibody carbohydrates by oxidation, conjugation, or deoxymannojirimycin does not interfere with antibody effector functions. Cancer Immunol Immunother. Jan. 1994;38(1):23-30.
Axford et al., Changes in normal glycosylation mechanisms in autoimmune rheumatic disease. J Clin Invest. Mar. 1992;89(3):1021-31.
Beck et al., Trends in glycosylation, glycoanalysis and glycoengineering of therapeutic antibodies and Fc-fusion proteins. Curr Pharm Biotechnol. Dec. 2008;9(6):482-501.
Bendig, Humanization of Rodent Monoclonal Antibodies by CDR Grafting. Companion to Methods in Enzymology. 1995;8:83-93.
Bird et al.,. Single-chain antigen-binding proteins. (1988) Science. 242: 423-426. Abstract only.
Black et al., Serum and secretory IgA from HIV-infected individuals mediate antibody-dependent cellular cytotoxicity. Clin Immunol Immunopathol. Nov. 1996;81(2):182-90.
Blanchard et al., N-glycosylation and biological activity of recombinant human alpha1-antitrypsin expressed in a novel human neuronal cell line. Biotechnol Bioeng. Sep. 2011;108(9):2118-28. doi: 10.1002/bit.23158. Epub Apr. 20, 2011.
Bookman et al., Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. J Clin Oncol. Jan. 15, 2003;21(2):283-90.
Borsig et al., Heparin and cancer revisited: mechanistic connections involving platelets, P-selectin, carcinoma mucins, and tumor metastasis. Proc Natl Acad Sci U S A. Mar. 13, 2001;98(6):3352-7.
Bosques et al., Chinese hamster ovary cells can produce galactose-?-1,3-galactose antigens on proteins. Nat Biotechnol. Nov. 2010;28(11):1153-6. doi: 10.1038/nbt1110-1153. Author manuscript.
Boyd et al., The effect of the removal of sialic acid, galactose and total carbohydrate on the functional activity of Campath-1H. Mol Immunol. Dec. 1995;32(17-18):1311-8.
Cabanes-Macheteau et al., N-Glycosylation of a mouse IgG expressed in transgenic tobacco plants. Glycobiology. Apr. 1999;9(4):365-72.
Campbell et al., Nuclear-cytoplasmic interactions during the first cell cycle of nuclear transfer reconstructed bovine embryos: implications for deoxyribonucleic acid replication and development. Biology of Reproduction. 1993;49(5):933-42.
Canfield et al., The binding affinity of human IgG for its high affinity Fc receptor is determined by multiple amino acids in the CH2 domain and is modulated by the hinge region. J Exp Med. 1991;173(6):1483-91.
Carter, Introduction to current and future protein therapeutics: a protein engineering perspective. Exp Cell Res. May 15, 2011;317(9):1261-9. Doi: 10.1016/j.yexcr.2011.02.013. Epub Mar. 1, 2011.
Carton et al., Codon engineering for improved antibody expression in mammalian cells. Protein Expr Purif. Oct. 2007;55(2):279-86. Epub Jun. 16, 2007.
Cartron et al., Therapeutic activity of humanized anti-CD20 monoclonal antibody and polymorphism in IgG Fc receptor FcgammaRIIIa gene. Blood. Feb. 1, 2002;99(3):754-8.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012. Author manuscript.
Chitlaru et al., Modulation of circulatory residence of recombinant acetylcholinesterase through biochemical or genetic manipulation of sialylation levels. Biochem J. Dec. 15, 1998;336 (Pt 3):647-58.
Chitlaru et al., Overloading and removal of N-glycosylation targets on human acetylcholinesterase: effects on glycan composition and circulatory residence time. Biochem J. May 1, 2002;363(Pt 3):619-31.
Chiu et al., In vivo targeting function of N-linked oligosaccharides with terminating galactose and N-acetylgalactosamine residues. J Biol Chem. Jun. 10, 1994;269(23):16195-202.
Cianga P, et al. Identification and function of neonatal Fc receptor in mammary gland of lactating mice. Eur J Immunol. 1999; 29:2515-23.
Clark et al., Assessing unintended effects of a mammary-specific transgene at the whole animal level in host and non-target animals. Transgenic Research. 2014;23:245-256.
Clark et al., Protein Purification of Bio-Synthetic Spider Silk. Utah State University. Apr. 2012. Available online at https://works.bepress.com/candace_clark/2/. Last accessed on Jan. 30, 2018. 2 pages.
Clynes et al., Fc receptors are required in passive and active immunity to melanoma. Proc Natl Acad Sci U S A. Jan. 20, 1998;95(2):652-6.
Clynes et al., Inhibitory Fc receptors modulate in vivo cytoxicity against tumor targets. Nat Med. Apr. 2000;6(4):443-6.
Colcher et al., Effects of Genetic Engineering on the Pharmacokinetics of Antibodies. QJ Nucl Med 1999; 43:132-9.
Cole et al. Glycosylation Patterns of Human Proteins Expressed in Transgenic Goat Milk. Journal of Cellular Biochemistry. 1994, Suppl. 18D, p. 265, Ab. U100, published online Feb. 19, 1994.
Commins et al., Anaphylaxis syndromes related to a new mammalian cross-reactive carbohydrate determinant. J Allergy Clin Immunol. Oct. 2009; 124(4):652-7.
Commins et al., Delayed anaphylaxis, angioedema, or urticaria after consumption of red meat in patients with IgE antibodies specific for galactose-alpha-1,3-galactose. J Allergy Clin Immunol. Feb. 2009;123(2):426-33.
Crowe et al., Humanized Monoclonal Antibody Campath-1H: Myeloma Cell Expression of Genomic Constructs, Nucleotide Sequence of cDNA Constructs and Comparison of Effector Mechanisms of Myeloma and Chinese Hamster Ovary Cell Derived Material. Clin Exp Immunol. Jan. 1992;87(1):105-10.
Dai et al., Targeted Disruption of the α1,3-Galactosyltransferase Gene in Cloned Pigs. Nature Biotechnology. Mar. 2002;20:251-5.
Dall'Ozzo et al., Rituximab-dependent cytotoxicity by natural killer cells: influence of FCGR3A polymorphism on the concentration-effect relationship. Cancer Res. Jul. 1, 2004;64(13):4664-9.
Dalziel et al., Mouse ST6Gal Sialytransferase Gene Expression During Mammary Glad Lactation. Glycobiology. May 1, 2001;11(5):407-12.
Davies et al., Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.
Davis et al., Single Chain Antibody (SCA) Encoding Genes: One-Step Construction and Expression in Eukaryotic Cells. Bio/Technol. 1991;9:165-69.
DeFazio-Eli et al., Quantitative assays for the measurement of HER1-HER2 heterodimerization and phosphorylation in cell lines and breast tumors: applications for diagnostics and targeted drug mechanism of action. Breast Cancer Res. Apr. 15, 2011;13(2):R44.
Dorai et al., Aglycosylated chimeric mouse/human IgG1 antibody retains some effector function. Hybridoma. Apr. 1991;10(2):211-7.
Edmunds et al., Tissue Specific and Species Differences in the Glycosylation Pattern of Antithrombin III, Journal of Cellular Biochemistry, Abstract U102, pp. 265 (1994).

(56) References Cited

OTHER PUBLICATIONS

Edmunds et al., Transgenically produced human antithrombin: structural and functional comparison to human plasma-derived antithrombin. Blood. Jun. 15, 1998; 91 (12): 4561-4571.
Fan et al., Heterogeneity of recombinant human antithrombin III expressed in baby hamster kidney cells. Effect of glycosylation differences on heparin binding and structure. J Biol Chem. Aug. 15, 1993;268(23):17588-96.
Federspiel et al., Hybridoma Antibody Production In Vitro in Type II Serum-Free Medium Using Nutridoma-SP Supplements: Comparisons With In Vivo Methods. J Immunol Methods. 1991;145(1-2):213-221.
Fernandes, Demonstrating Comparability of Antibody Glycosylation during Biomanufacturing. European Biopharmaceutical Review. Summer 2005: 106-10.
Finck et al., Treatment of murine lupus with CTLA4Ig. Science. Aug. 26, 1994;265(5176):1225-7.
Fliedl et al., Novel Human Renal Proximal Tubular Cell Line for the Production of Complex Proteins. Journal of Biotechnology. 2014;176:29-39.
Forthal et al., Recombinant gp120 vaccine-induced antibodies inhibit clinical strains of HIV-1 in the presence of Fc receptor-bearing effector cells and correlate inversely with HIV infection rate. J Immunol. May 15, 2007;178(10):6596-603.
Fujii et al., Structural heterogeneity of sugar chains in immunoglobulin G. Conformation of immunoglobulin G molecule and substrate specificities of glycosyltransferases. J Biol Chem. Apr. 15, 1990;265(11):6009-18.
Galeotti et al., [Intravenous immunoglobulins in autoimmune and inflammatory disorders: beyond a simple substitution]. Transfus Clin Biol. May 2009;16(2):75-9. doi: 10.1016/j.tracli.2009.03.009. Epub May 13, 2009. Article in French.
Gee et al., Human breast cancer tumor models: molecular imaging of drug susceptibility and dosing during HER2/neu-targeted therapy. Radiology. Sep. 2008;248(3):925-35.
Ghetie et al., FcRn: the MHC class I-related receptor that is more than an IgG transporter. Immunol Today. Dec. 1997;18(12):592-8.
Gil et al., Analysis of the N-glycans of recombinant human Factor IX purified from transgenic pig milk. Glycobiology. Jul. 2008;18(7):526-39.
Goeddel, Systems for Heterologous Gene Expression. Methods in Enzymology. 1990;185:3-7.
Goodarzi et al., Decreased branching, increased fucosylation and changed sialylation of alpha-1-proteinase inhibitor in breast and ovarian cancer. Clin Chim Acta. May 15, 1995;236(2):161-71.
Gottlieb et al., Deficient uridine diphosphate-N-acetylglucosamine:glycoprotein N-acetylglucosaminyltransferase activity in a clone of Chinese hamster ovary cells with altered surface glycoproteins. J Biol Chem. May 10, 1975;250(9):3303-9.
Gramer et al., Modulation of antibody galactosylation through feeding of uridine, manganese chloride, and galactose. Biotechnol Bioeng. Jul. 2011;108(7):1591-602. doi: 10.1002/bit.23075. Epub Feb. 18, 2011.
Grönlund et al., The carbohydrate galactose-alpha-1,3-galactose is a major IgE-binding epitope on cat IgA. J Allergy Clin Immunol. May 2009;123(5):1189-91.
Guerrier et al., A dual-mode approach to the selective separation of antibodies and their fragments. J Chromatogr B Biomed Sci Appl. May 5, 2001;755(1-2):37-46.
Guile et al., A rapid high-resolution high-performance liquid chromatographic method for separating glycan mixtures and analyzing oligosaccharide profiles. Anal Biochem. Sep. 5, 1996;240(2):210-26.
Ha et al., Isolation and characterization of IgG1 with asymmetrical Fc glycosylation. Glycobiology. Aug. 2011;21(8):1087-96. doi: 10.1093/glycob/cwr047. Epub Apr. 5, 2011.
Hand et al., Comparative biological properties of a recombinant chimeric anti-carcinoma mAb and a recombinant aglycosylated variant. Cancer Immunol Immunother. 1992;35(3):165-74.
Harduin-Lepers et al., The human sialyltransferase family. Biochimie. Aug. 2001;83(8):727-37.
Hauschild et al., Efficient Generation of a Biallelic Knockout in Pigs Using Zinc-Finger Nucleases. PNAS. Jul. 19, 2011;108(29):12013-12017.
Hellström et al., T cell immunity to tumor antigens. Crit Rev Immunol. 1998;18(1-2):1-6.
Hernandez-Ilizaliturri et al., Neutrophils contribute to the biological antitumor activity of rituximab in a non-Hodgkin's lymphoma severe combined immunodeficiency mouse model. Clin Cancer Res. Dec. 1, 2003;9(16 Pt 1):5866-73.
Hishii et al., Studies of the mechanism of cytolysis by tumour-infiltrating lymphocytes. Clin Exp Immunol. Jun. 1999;116(3):388-94.
Hobbs et al., Complex Hormonal Regulation of Rat Casein Gene Expression. Journal of Biological Chemistry. Apr. 10, 1982;257(7):3598-605.
Hodoniczky et al., Control of recombinant monoclonal antibody effector functions by Fc N-glycan remodeling in vitro. Biotechnol Prog. Nov.-Dec. 2005;21(6):1644-52.
Holl et al., Antibody-Mediated Fc? Receptor-Based Mechanisms of HIV Inhibition: Recent Findings and New Vaccination Strategies. Viruses. Dec. 2009;1(3):1265-94. doi: 10.3390/v1031265. Epub Dec. 15, 2009.
Holliger et al., Diabodies: small bivalent and bispecific antibody fragments. Proc. Natl. Acad. Sci. USA. 1993;90:6444-6448.
Holliger et al., Engineered antibody fragments and the rise of single domains. Nat Biotechnol. Sep. 2005;23(9):1126-36.
Hong et al., A humanized anti-4-1BB monoclonal antibody suppresses antigen-induced humoral immune response in nonhuman primates. J Immunother. Nov.-Dec. 2000;23(6):613-21.
Hong et al., Substitution of glutamine by glutamate enhances production and galactosylation of recombinant IgG in Chinese hamster ovary cells. Appl Microbiol Biotechnol. Oct. 2010;88(4):869-76. doi: 10.1007/s00253-010-2790-1. Epub Aug. 3, 2010.
Horwitz et al., Secretion of functional antibody and Fab fragment from yeast cells. Proc Natl Acad Sci U S A. Nov. 1988;85(22):8678-82.
Houde et al., Post-translational modifications differentially affect IgG1 conformation and receptor binding. Molecular & Cellular Proteomics. Aug. 2010;9(8):1716-28.
Houot et al., Boosting antibody-dependant cellular cytotoxicity against tumor cells with a CD137 stimulatory antibody. Oncoimmunology. Sep. 1, 2012;1(6):957-958.
Humphreys et al., Therapeutic antibody production technologies: molecules, applications, expression and purification. Curr Opin Drug Discov Devel. Mar. 2001;4(2):172-85.
Huston et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Jacquenet et al., Mammalian meat-induced anaphylaxis: clinical relevance of anti-galactose-alpha-1,3-galactose IgE confirmed by means of skin tests to cetuximab. J Allergy Clin Immunol. Sep. 2009;124(3):603-5.
Jain et al., Targeted inactivation of G?1 does not alter cardiac function or ?-adrenergic sensitivity. Am J Physiol Heart Circ Physiol. 2001;280:H569-H575.
James et al., N-glycosylation of recombinant human interferon-gamma produced in different animal expression systems. Biotechnology (N Y). Jun. 1995;13(6):592-6.
Jefferis et al., Recognition sites on human IgG for Fc gamma receptors: the role of glycosylation. Immunol Lett. 1995;44(2-3):111-7.
Jefferis, Glycolisation of human IgG antibodies: Relevance to therapeutic applications. Biopharm. Sep. 2001;14(9):19-27.
Jefferis, Glycosylation of Recombinant IgG Antibodies and Its Relevance for Therapeutic Applications. Cell Engineering. 2002;3:93-107.
Jeong et al., Enhanced sialylation of recombinant erythropoietin in CHO cells by human glycosyltransferase expression. J Microbiol Biotechnol. Dec. 2008;18(12):1945-52.

(56) References Cited

OTHER PUBLICATIONS

Jones et al., Ectopic Correction of Ornithine Transcarbamylase Deficiency in Sparse Fur Mice. Journal of Biological Chemistry. Aug. 25, 1990;265(24):14684-14690.

Jung et al., Aglycosylated IgG variants expressed in bacteria that selectively bind FcgammaRI potentiate tumor cell killing by monocyte-dendritic cells. Proc Natl Acad Sci U S A. Jan. 12, 2010;107(2):604-9. Epub Dec. 18, 2009. Abstract only.

Junghans et al., The protection receptor for IgG catabolismis the ?2-microglobulin-containing neonatal intestinal transport receptor. Proc. Natl. Acad. Sci. USA. 1996;93(11):5512-6.

Junghans, Finally! The Brambell Receptor (FcRB): Mediator of Transmission of Immunity and Protection from Catabolismfor IgG. Immunol Res. Feb. 1997;16(1):29-57.

Kacskovics, Fc receptors in livestock species. Vet Immunol Immunopathol. Dec. 28, 2004;102(4):351-62.

Kasinathan et al., Effect of Fibroblast Donor Cell Age and Cell Cycle on Development of Bovine Nuclear Transfer Embryos in Vitro. Biology of Reproduction. 2001;64:1487-1493.

Kerr et al., The bladder as a bioreactor: Urothelium production and secretion of growth hormone into urine. Nature Biotechnology. Jan. 1998; 16(1):75-9.

Kim et al., Catabolismof the murine IgG1 molecule: evidence that both CH2-CH3 domain interfaces are required for persistence of IgG1 in the circulation of mice. Scand J Immunol. 1994;40(4):457-65.

Kipps et al., Importance of immunoglobulin isotype in human antibody-dependent, cell-mediated cytotoxicity directed by murine monoclonal antibodies. J Exp Med. Jan. 1, 1985;161(1):1-17.

Koene et al., Fc gammaRIIIa-158V/F polymorphism influences the binding of IgG by natural killer cell Fc gammaRIIIa, independently of the Fc gammaRIIIa-48L/R/H phenotype. Blood. Aug. 1, 1997;90(3):1109-14.

Köhler et al., Continuous cultures of fused cells secreting antibody of predefined specificity. Nature. Aug. 7, 1975;256(5517):495-7.

Kumpel et al., Galactosylation of human IgG monoclonal anti-D produced by EBV- transformed B-lymphoblastoid cell lines is dependent on culture method and affects Fc receptor-mediated functional activity. Hum Antibodies Hybridomas. 1994;5(3-4): 143-51.

Labrou, Protein purification: an overview. Methods Mol Biol. 2014;1129:3-10. doi: 10.1007/978-1-62703-977-2_1.

Lang et al., Chimeric CD19 antibody mediates cytotoxic activity against leukemic blasts with effector cells from pediatric patients who received T-cell-depleted allografts. Blood. May 15, 2004;103(10):3982-5. Epub Feb. 5, 2004.

Lanteri et al., Designing a HER2/neu Promotor to Drive ?1,3Galactosyltransferase Expression for Targeted Anti-?Galantibody-Mediated Tumor Cell Killing. Breast Cancer Research. 2005;7:R487-94.

Lantto et al., Chain Shuffling to Modify Properties of Recombinant Immunoglobulins. Methods Mol. Biol. (2002) 178: 303-316.

Leach J. L. et al., Isolation from Human Placenta of the IgG Transporter, FcRn, and Localization to the Syncytiotrophoblast: Implications for Maternal-Fetal Antibody Transport, J. Immunology, (1996) 157(8): 3317-3322.

Leatherbarrow et al., Effector functions of a monoclonal aglycosylated mouse IgG2a: binding and activation of complement component C1 and interaction with human monocyte Fc receptor. Mol Immunol. 1985;22(4):407-15.

Lee et al., Production of biomedical proteins in the milk of transgenic dairy cows: the state of the art. Journal of Controlled Release. 1994;29:213-231.

Li et al., Biallelic Knockout of the ?-1,3 Galactosyltransferase Gene in Procine Liver-Derived Cells Using Zinc Finger Nucleases. Journal of Surgical Research. 2013; 181:E39-E45.

Li et al., Structure of the altered oligosaccharide present in glycoproteins from a clone of Chinese hamster ovary cells deficient in N-acetylglucosaminyltransferase activity. J Biol Chem. Sep. 25, 1978;253(18):6426-31.

Liao et al., Design of Transgenes for Efficient Expression of Active Chimeric Proteins on Mammalian Cells. Biotechnology and Bioengineering. May 20, 2001;73(4):313-23.

Lifely et al., Glycosylation and biological activity of Campath-1H expressed in different cell lines and grown under different culture conditions. Glycobiology. Dec. 1995;5(8):813-22.

Lin et al., Fc-dependent expression of CD137 on human NK cells: insights into "agonistic" effects of anti-CD137 monoclonal antibodies. Blood. Aug. 1, 2008;112(3):699-707. Epub Jun. 2, 2008.

Listinsky et al., P2-18-06: Conventional Trastuzumab is an Antagonist of Natural Killer Cells: Making the Case for Fucose-Depleted Trastuzumab. Cancer Res. 2011;71(24 Suppl): Abstract nr P2-18-06.

Liu et al., A comparison of herpes simplex virus specific antibodies found in human milk and serum. Pediatr Res. Jun. 1992;31(6):591-5.

Louis et al., Association between polymorphism in IgG Fc receptor IIIa coding gene and biological response to infliximab in Crohn's disease. Aliment Pharmacol Ther. Mar. 1, 2004;19(5):511-9.

Lu et al., Over-expression of the bovine FcRn in the mammary gland results in increased IgG levels in both milk and serum of transgenic mice. Immunology. 2007;122(3):401-408.

Lund et al., Control of IgG/Fc glycosylation: a comparison of oligosaccharides from chimeric human/mouse and mouse subclass immunoglobulin Gs. Mol Immunol. 1993;30(8):741-8.

Lund et al., Multiple interactions of IgG with its core oligosaccharide can modulate recognition by complement and human Fc gamma receptor I and influence the synthesis of its oligosaccharide chains. J Immunol. 1996; 157(11):4963-9.

Lund et al., Oligosaccharide-protein interactions in IgG can modulate recognition by Fc gamma receptors. FASEB J. Jan. 1995;9(1):115-9.

Lusch et al., Development and Analysis of Alpha 1-Antitrypsin Neoglycoproteins: The Impact of Additional N-Glycosylation Sites on Serum Half-Life. Molecular Pharmaceutics. Jul. 1, 2013;10(7)2616-29.

Magdelaine-Beuzelin et al., Structure-function relationships of the variable domains of monoclonal antibodies approved for cancer treatment. Crit Rev Oncol Hematol. Dec. 2007;64(3):210-25.

Malaise et al., Evidence for a role of accessible galactosyl or mannosyl residues of Fc domain in the in vivo clearance of IgG antibody-coated autologous erythrocytes in the rat. Clin Immunol Immunopathol. 1990;54(3):469-83.

Mattu et al., The glycosylation and structure of human serum IgA1, Fab, and Fc regions and the role of N-glycosylation on Fc alpha receptor interactions. J Biol Chem. Jan. 23, 1998;273(4):2260-72.

Mayer et al., Redistribution of the sheep neonatal Fc receptor in the mammary gland around the time of parturition in ewes and its localization in the small intestine of neonatal lambs. Immunology. Nov. 2002;107(3):288-96.

Maynard et al., Antibody engineering. Annu Rev Biomed Eng. 2000;2:339-76.

McGrane et al., Matebolic control of gene expression: in vivo studies with transgenic mice. Trands Biochem Sci. Jan. 1992;17(1):40-44.

Mimura et al., Role of Oligosaccharide residues of IgG1-Fc in Fc gamma RIIb binding. J Biol Chem 2001; 276(49): 45539-47.

Mimura et al., The influence of glycosylation on the thermal stability and effector function expression of human IgG1-Fc: properties of a series of truncated glycoforms. Mol Immunol. 2000;37(12-13):697-706.

Morgan et al., Designing Biobetter Monoclonal Antibody Therapeutics by Glycoengineering. International Pharmaceutical Industry. 2009. 5 pages.

Morisset et al., Anaphylaxis to pork kidney is related to IgE antibodies specific for galactose-alpha-1,3-galactose. Allergy. May 2012;67(5):699-704.

Nagy et al., Targeted mutagenesis: analysis of phenotype without germ line transmission. J Clin Invest. Mar. 15, 1996;97(6):1360-1365.

Nair et al., Epitope recognition by diverse antibodies suggests conformational convergence in an antibody response. J Immunol. Mar. 1, 2002;168(5):2371-82.

(56) References Cited

OTHER PUBLICATIONS

Niemann et al., Transgenic Livestock: premises and promises. Animal Reproduction Science. 2000;60-61:277-293.

Niwa et al., Defucosylated chimeric anti-CC chemokine receptor 4 IgG1 with enhanced antibody-dependent cellular cytotoxicity shows potent therapeutic activity to T-cell leukemia and lymphoma. Cancer Res. Mar. 15, 2004;64(6):2127-33.

Niwa et al., Enhanced natural killer cell binding and activation by low-fucose IgG1 antibody results in potent antibody-dependent cellular cytotoxicity induction at lower antigen density. Clin Cancer Res. Mar. 15, 2005;11(6):2327-36.

Niwa et al., Enhancement of the antibody-dependent cellular cytotoxicity of low-fucose IgG1 Is independent of FcgammaRIIIa functional polymorphism. Clin Cancer Res. Sep. 15, 2004;10(18 Pt 1):6248-55.

Nose et al., Biological significance of carbohydrate chains on monoclonal antibodies. Proc Natl Acad Sci USA. 1983;80(21):6632-6.

Ober et al., Exocytosis of IgG as mediated by the receptor, FcRn: an analysis at the single-molecule level. Proc Natl Acad Sci USA. Jul. 27, 2004;101(30):11076-11081.

Ober et al., Differences in promiscuity for antibody-FcRn interactions across species: implications for therapeutic antibodies. Int Immunol. Dec. 2001;13(12):1551-9.

Okayama et al., A cDNA Cloning Vector That Permits Expression of cDNA Inserts in Mammalian Cells. Molecular and Cellular Biology. Feb. 1983;3(2):280-289.

Okazaki et al., Fucose depletion from human IgG1 oligosaccharide enhances binding enthalpy and association rate between IgG1 and FcgammaRIIIa. J Mol Biol. Mar. 5, 2004;336(5):1239-49.

Okemefuna et al., Complement factor H binds at two independent sites to C-reactive protein in acute phase concentrations. J Biol Chem. Jan. 8, 2010;285(2):1053-65. doi: 10.1074/jbc.M109.044529. Epub Oct. 22, 2009.

Ongeri et al., Development of Goat Embryos after in Vitro Fertilization and Parthenogenetic Activation by Different Methods. Theriogenology. 2001;55:1933-1945.

Onitsuka et al., Enhancement of sialylation on humanized IgG-like bispecific antibody by overexpression of ?2,6-sialyltransferase derived from Chinese hamster ovary cells. Appl Microbiol Biotechnol. Apr. 2012;94(1):69-80.

Ono et al., Production of anti-prion scFv-Fc fusion proteins by recombinant animal cells. J Biosci Bioeng. 2003;95(3):231-8.

Packer et al., A general approach to desalting oligosaccharides released from glycoproteins. Glycoconj J. Aug. 1998;15(8):737-47.

Padlan, Anatomy of the Antibody Molecule. Mol. Immunol. 1994;31(3):169-217.

Palombella et al., FCRN-mediated pulmonary delivery of interferon alpha FC-fusion protein in non-human primates. Hepatology, Williams and Wilkins, Baltimore, MD. vol. 38 (4) Suppl. 1, 2003, p. 277. Abstract.

Pangburn et al., Molecular mechanisms of target recognition in an innate immune system: interactions among factor H, C3b, and target in the alternative pathway of human complement. J Immunol. May 1, 2000;164(9):4742-51.

Papac et al., A high-throughput microscale method to release N-linked oligosaccharides from glycoproteins for matrix-assisted laser desorption/ionization time-of-flight mass spectrometric analysis. Glycobiology. 1998;8(5):445-454.

Parekh et al., Association of rheumatoid arthritis and primary osteoarthritis with changes in the glycosylation pattern of total serum IgG. Nature. 1985;316(6027):452-7.

Paul, Chapter 9: Fv Structure and Diversity in Three Dimensions. Fundamental Immunology, 3rd Edition. 1993: 292-5.

Pearse et al., Chapter 12: Anti-Xenograft Immune Responses in ?1,3-Galactosyltransferase Knock-Out Mice. In ?-Gal and Anti-Gal. 1999: 281-310.

Poljak et al., Production and structure of diabodies. Structure. 1994;2:1121-1123.

Pound et al., Aglycosylated chimaeric human IgG3 can trigger the human phagocyte respiratory burst. Mol Immunol. Feb. 1993;30(3):233-41.

Praetor et al., beta(2)-Microglobulin is important for cell surface expression and pH-dependent IgG binding of human FcRn. J Cell Sci. Jun. 1, 2002;115(Pt 11):2389-97.

Qian et al., Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion. Anal Biochem. May 1, 2007;364(1):8-18.

Rademacher et al., Glycobiology. Annu Rev Biochem. 1988;57:785-838.

Rademacher et al., Immunoglobulin G as a glycoprotein. Biochem Soc Symp. 1986;51:131-48.

Rademacher et al., The role of IgG glycoforms in the pathogenesis of rheumatoid arthritis. Springer Semin Immunopathol. 1988;10(2-3):231-49.

Rademacher, Glycosylation as a factor affecting product consistency. Biologicals. Jun. 1993;21(2):103-4.

Rafiq et al., Immune complex-mediated antigen presentation induces tumor immunity. J Clin Invest. Jul. 2002;110(1):71-9.

Raju, Glycosylation Variations with Expression Systems. BioProcess International. Apr. 2003; 44-53.

Raju, Terminal sugars of Fc glycans influence antibody effector functions of IgGs. Curr Opin Immunol. Aug. 2008;20(4):471-8. Epub Jul. 17, 2008.

Reff et al., Depletion of B cells in vivo by a chimeric mouse human monoclonal antibody to CD20. Blood. Jan. 15, 1994;83(2):435-45.

Regalado, Building a Better Goat. MIT Technology Review. Oct. 20, 2010. Available online at https://www.technologyreview.com/s/421268/building-a-better-goat/. Last accessed on Mar. 19, 2014. 2 pages.

Robak et al., New anti-CD20 monoclonal antibodies for the treatment of B-cell lymphoid malignancies. BioDrugs. Feb. 1, 2011;25(1):13-25. doi: 10.2165/11539590-000000000-00000.

Robak, GA-101, a third generation, humanized and glyco-engineered ant-CD20 mAb for the treatment of B-cell lymphoid malignancies. Current Opinion in Investigational Drugs. Jun. 2009;10(6):588-596.

Ross et al., Production and characterization of a novel human recombinant alpha-1-antitrypsin in PER.C6 cells. J Biotechnol. Dec. 31, 2012;162(2-3):262-73.

Rothman et al., Antibody-dependent cytotoxicity mediated by natural killer cells is enhanced by castanospermine-induced alterations of IgG glycosylation. Mol Immunol. Dec. 1989;26(12):1113-23.

Rudd et al., Diversification of the IgG molecule by oligosaccharides. Mol Immunol. Dec. 1991;28(12):1369-78.

Sakai et al., Recombination and transcription of the endogenous Ig heavy chain locus is effected by the Ig heavy chain itronic enhancer core region in the absence of the matrix attachment regions. Proc. Natl. Acad. Sci. USA. Feb. 1999;96:1526-1531.

Samuelsson et al., Anti-inflammatory activity of IVIG mediated through the inhibitory Fc receptor. Science. Jan. 19, 2001;291(5503):484-6.

Sazinsky et al., Aglycosylated immunoglobulin G1 variants productively engage activating Fc receptors. Proc Natl Acad Sci U S A. Dec. 23, 2008;105(51):20167-72. Epub Dec. 12, 2008. Abstract only.

Schuurman et al., The inter-heavy chain disulfide bonds of IgG4 are in equilibrium with intra-chain disulfide bonds. Mol Immunol. Jan. 2001;38(1):1-8.

Sendai et al., ?1,3-Galactosyltransferase-Gene Knockout in Cattle Using a Single Targeting Vector with IoxP Sequences and Cre-Expressing Adenovirus. Transplantation. Mar. 16, 2006;81(5):760-6.

Shen et al., Tissue-Specific Regulation of Human ?1-Antitrypsin Gene Expression in Transgenic Mice. DNA. 1989;8(2):101-108.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. Epub Nov. 28, 2000.

(56) References Cited

OTHER PUBLICATIONS

Shields et al., Lack of fucose on human IgG1 N-linked oligosaccharide improves binding to human Fcgamma RIII and antibody-dependent cellular toxicity. J Biol Chem. Jul. 26, 2002;277(30):26733-40. Epub May 1, 2002.

Shim, One target, different effects: a comparison of distinct therapeutic antibodies against the same targets. Exp Mol Med. Oct. 31, 2011;43(10):539-49. doi: 10.3858/emm.2011.43.10.063.

Shimada et al., Correction of ornithine transcarbamylase (OTC) deficiency in spf-ash mice by introduction of rat OTC gene. FEBS letters. Feb. 1991;279(1):198-200.

Shinkawa et al., The Absence of Fucose but Not the Presence of Galactose or Bisecting N-Acetylglucosamine of Human IgG 1 Complex-type Oligosaccharides Shows the Critical Role of Enhancing Antibody-dependent Cellular Cytotoxicity. J Biol Chem. Jan. 2003;278(5):3466-73.

Simmons et al., Expression of full-length immunoglobulins in *Escherichia coli*: rapid and efficient production of aglycosylated antibodies. J Immunol Methods. May 1, 2002;263(1-2):133-47.

Stanley et al., Chinese hamster ovary cells selected for resistance to the cytotoxicity of phytohemagglutinin are deficient in a UDP-N-acetylglucosamine—glycoprotein N-acetylglucosaminyltransferase activity. Proc Natl Acad Sci U S A. Sep. 1975;72(9):3323-7.

Stanley, Glycosylation mutants of animal cells. Annu Rev Genet. 1984;18:525-52.

Stockwin et al., The role of therapeutic antibodies in drug discovery. Biochem Soc Trans. 2003;31(2):433-6.

Suen et al., Transient expression of an IL-23R extracellular domain Fc fusion protein in CHO vs. HEK cells results in improved plasma exposure. Protein Expr Purif. May 2010;71(1):96-102. doi: 10.1016/j.pep.2009.12.015. Epub Jan. 4, 2010.

Sumar et al., Analysis of glycosylation changes in IgG using lectins. J Immunol Methods. Jul. 20, 1990;131(1):127-36.

Sutton et al., The three-dimensional structure of the carbohydrate within the Fc fragment of immunoglobulin G. Biochem Soc Trans. Apr. 1983;11 Pt 2:130-2.

Takeuchi et al., A novel mutation in the FcgammaRIIIA gene (CD16) results in active natural killer cells lacking CD16. Autoimmunity. 1999;31(4):265-71.

Tamamori et al., Granulocyte-colony stimulating factor enhances chimeric antibody Nd2 dependent cytotoxicity against pancreatic cancer mediated by polymorphonuclear neutrophils. Int J Oncol. Sep. 2002;21(3):649-54.

Tan et al., Influence of the hinge region on complement activation, C1q binding, and segmental flexibility in chimeric human immunoglobulins. Proc Natl Acad Sci U S A. Jan. 1990;87(1):162-6.

Tan, Liver-Specific and Position-Effect Expression of a Retinol-Binding Protein-lacZ Fusion Gene (RBP-lacZ) in Transgenic Mice. Developmental Biology. 1991:146:24-37.

Tandai et al., Structural study of the sugar moieties of monoclonal antibodies secreted by human-mouse hybridoma. Arch Biochem Biophys. 1991;291(2):339-48.

Tao et al., Studies of aglycosylated chimeric mouse-human IgG. Role of carbohydrate in the structure and effector functions mediated by the human IgG constant region. J Immunol. Oct. 15, 1989;143(8):2595-601.

Thomann et al., Fc-galactosylation modulates antibody-dependent cellular cytotoxicity of therapeutic antibodies. Molecular Immunology. 2016;73:69-75.

Thornburg et al., Carbohydrate-mediated clearance of immune complexes from the circulation. A role for galactose residues in the hepatic uptake of IgG-antigen complexes. J Biol Chem. Jul. 25, 1980;255(14):6820-5.

Todorovska et al., Design and application of diabodies, triabodies and tetrabodies for cancer targeting. J Immunol Methods. Feb. 1, 2001;248(1-2):47-66.

Topalian et al., Tumor-specific cytolysis by lymphocytes infiltrating human melanomas. J Immunol. May 15, 1989;142(10):3714-25.

Toyama et al., Quantitative structural characterization of local N-glycan microheterogeneity in therapeutic antibodies by energy-resolved oxonium ion monitoring. Analytical Chem. Nov. 20, 2012;84(22):9655-62.

Treon et al., Polymorphisms in FcgammaRIIIA (CD16) receptor expression are associated with clinical response to rituximab in Waldenström's macroglobulinemia. J Clin Oncol. Jan. 20, 2005;23(3):474-81.

Tsuchiya et al., Effects of galactose depletion from oligosaccharide chains on immunological activities of human IgG. J Rheumatol. 1989;16(3):285-90.

Varchetta et al., Elements related to heterogeneity of antibody-dependent cell cytotoxicity in patients under trastuzumab therapy for primary operable breast cancer overexpressing Her2. Cancer Research. Dec. 15, 2007;67(24):1191-9.

Walker et al., Aglycosylation of human IgG1 and IgG3 monoclonal antibodies can eliminate recognition by human cells expressing Fc gamma RI and/or Fc gamma RII receptors. Biochem J. Apr. 15, 1989;259(2):347-53.

Ward et al., Characterization of humanized antibodies secreted by Aspergillus niger. Appl Environ Microbiol. May 2004;70(5):2567-76.

Watson et al., Molecular Biology of the Gene. 4th edition. Chapter 19: Recombinant DNA at Work. The Benjamin/Cummings Publishing Company, Inc. Menlo Park, California. 1987:595-618.

Weidle et al., Genes encoding a mouse monoclonal antibody are expressed in transgenic mice, rabbits and pigs. Gene. Feb. 15, 1991;98(2):185-91.

Wells et al., Production of Cloned Calves Following Nuclear Transfer with Cultured Adult Mural Granulosa Cells. Biology of Reproduction. 1999;60:996-1005.

Werner et al., Glycosylation of therapeutic proteins in different production systems. Acta Paediatr. Apr. 2007;96(455):17-22.

Wilkins et al., Isolation of Recombinant Proteins From Milk. Journal of Cellular Biochemistry. 1992;49:333-338.

Wold, In vivo chemical modification of proteins (post-translational modification). Ann Rev Biochem. 1981;50:783-814.

Wolfgang et al., Efficient Method for Expressing Transgenes in Nonhuman Primate Embryos Using a Stable Episomal Vector. Molecular Reproduction and Development. 2002;62:69-73.

Wright et al., Effect of C2-associated carbohydrate structure on Ig effector function: studies with chimeric mouse-human IgG1 antibodies in glycosylation mutants of Chinese hamster ovary cells. J Immunol. Apr. 1, 1998;160(7):3393-402.

Wright et al., High Level Expression of Active Human Alpha-1-Antitrypsin in the Milk of Transgenic Sheep. Biotechnology. 1991;9:830-834.

Yamane-Ohnuki et al., Establishment of FUT8 knockout Chinese hamster ovary cells: an ideal host cell line for producing completely defucosylated antibodies with enhanced antibody-dependent cellular cytotoxicity. Biotechnol Bioeng. Sep. 5, 2004;87(5):614-22.

Yong et al., Nuclear-Cytoplasmic Interaction and Development of Goat Embryos Reconstructed by Nuclear Transplantation: Production of Goats by Serially Cloning Embryos. Biology of Reproduction. 1998;58:266-269.

Yu et al., Functional Human CD4 Protein Produced in Milk of Transgenic Mice. Mol Biol Med. 1989;6:255-261.

Yung et al., Complete absence of the ?Gal xenoantigen and isoglobotrihexosylceramide in ?1,3galactosyltransferase knock-out pigs. Xenotransplantation. May-Jun. 2012;19(3):196-206.

Zbikowska et al., The use of uromodulin promoter to target production of recombinant proteins into urine of transgenic animals. Transgenic Research. 2002;11:425-435.

Zbikowska et al., Uromodulin promoter directs high-level expression of biologically active human ?1-antitrypsin into mouse urine. Biochem J. 2002;365:7-11.

Zhang et al., Functional Recombinant Human Anti-HBV Antibody Expressed in Milk of Transgenic Mice. Transgenic Res. 2012;21:1085-91.

Zhou et al., Development of a simple and rapid method for producing non-fucosylated oligomannose containing antibodies with increased effector function. Biotechnol Bioeng. Feb. 15, 2008;99(3):652-65.

(56) References Cited

OTHER PUBLICATIONS

Zhou et al., Effect of genetic background on glycosylation heterogeneity in human antithrombin produced in the mammary gland of transgenic goats. J Biotechnol. Apr. 20, 2005;117(1):57-72.
Ziomek, Commercialization of Proteins Produced in the Mammary Gland. Theriogenology. 1998;49:139-44.
Jenkins et al., Getting the glycosylation right: implications for the biotechnology industry. Nat Biotechnol. Aug. 1996;14(8):975-81. doi: 10.1038/nbt0896-975.
Van Beuren et al., Anti-galactose-α-1,3-galactose IgE from allergic patients does not bind α-galactosylated glycans on intact therapeutic antibody Fc domains. Nat Biotechnol. Jul. 11, 2011;29(7):574-6. doi: 10.1038/nbt.1912.
Article 94(3) mailed Dec. 22, 2020 for European Application No. EP 16747826.2.
Bas et al., Fc Sialylation Prolongs Serum Half-Life of Therapeutic Antibodies. J Immunol. Mar. 1, 2019;202(5):1582-1594. doi: 10.4049/jimmunol.1800896. Epub Jan. 25, 2019.
Goetze et al., High-mannose glycans on the Fc region of therapeutic IgG antibodies increase serum clearance in humans. Glycobiology. Jul. 2011;21(7):949-59. doi: 10.1093/glycob/cwr027. Epub Mar. 18, 2011.
Mondon et al., An innovative monomeric Fc fragment with high binding to FcRn and Fc gamma receptors for the treatment of autoimmune diseases. 7th Antibody Industrial Symposium 2019. Research Gate. Jun. 25, 2019. doi: 10.13140/RG.2.2.29444.37760. 23 pages.
Monnet et al., Selection of IgG Variants with Increased FcRn Binding Using Random and Directed Mutagenesis: Impact on Effector Functions. Front Immunol. Feb. 4, 2015;6:39. doi: 10.3389/fimmu.2015.00039.
Rath et al., Fc-fusion proteins and FcRn: structural insights for longer-lasting and more effective therapeutics. Crit Rev Biotechnol. Jun. 2015;35(2):235-54. doi: 10.3109/07388551.2013.834293. Epub Oct. 24, 2013.
Hermentin et al., The hypothetical N-glycan charge: a No. that characterizes protein glycosylation. Glycobiology. Mar. 1996;6(2):217-30. doi: 10.1093/glycob/6.2.217. PMID: 8727793.
Persson et al., Ca2+ binding to the first epidermal growth factor-like domain of factor VIIa increases amidolytic activity and tissue factor affinity. J Biol Chem. Aug. 8, 1997;272(32):19919-24.
Persson. Characterization of the interaction between the light chain of factor VIIa and tissue factor. FEBS Lett. Aug. 18, 1997;413(2):359-63. doi: 10.1016/s0014-5793(97)00941-1.
Qu et al., Bispecific anti-CD20/22 antibodies inhibit B-cell lymphoma proliferation by a unique mechanism of action. Blood. Feb. 15, 2008;111(4):2211-9. doi: 10.1182/blood-2007-08-110072. Epub Nov. 19, 2007. PMID: 18025153; PMCID: PMC2234056.
Ridgway et al., 'Knobs-into-holes' engineering of antibody CH3 domains for heavy chain heterodimerization. Protein Eng. Jul. 1996;9(7):617-21. doi: 10.1093/protein/9.7.617. PMID: 8844834.
Wright et al., Effect of altered CH2-associated carbohydrate structure on the functional properties and in vivo fate of chimeric mouse-human immunoglobulin G1. J Exp Med. Sep. 1, 1994;180(3):1087-96.
Mullard, A., FDA Approves drug from transgenic chicken. Nat. Reviews Drug Discovery. Published online Dec. 31, 2015. 1 page.
Lenting et al., Emicizumab, a bispecific antibody recognizing coagulation factors IX and X: how does it actually compare to factor VIII? Blood. Dec. 7, 2017;130(23):2463-2468. doi: 10.1182/blood-2017-08-801662. Epub Oct. 17, 2017.
Monnet et al., Combined glyco- and protein-Fc engineering simultaneously enhance cytotoxicity and half-life of a therapeutic antibody. MAbs. Mar.-Apr. 2014;6(2):422-36. doi: 10.4161/mabs.27854. Epub Jan. 15, 2014.
Monnet et al., The Dual Targeting of FcRn and FcγRs via Monomeric Fc Fragments Results in Strong Inhibition of IgG-Dependent Autoimmune Pathologies. Front Immunol. Aug. 26, 2021:12:728322. doi: 10.3389/fimmu.2021.728322. eCollection 2021.

\* cited by examiner

```
                                                                                         226
                                                                                          →
IgG1m(1,17)    EPKSCDK--THT----------------------------------------CPPC...
IgG1m(3)       EPKSCDK--THT----------------------------------------CPPC...
IgG2           ERKCCVE---------------------------------------------CPPC...
IgG3           ELKTPLGDTTHTCPRCPEPKSCDTPPPCPRCPEPKSCDTPPPCPRCPEPKSCDTPPPCPRC...
IgG4           ESKYG-----------------------------------------------PPCPSCP...

IgG1m(1,17)    [shaded sequence]
IgG1m(3)       [shaded sequence]
IgG2           [shaded sequence]
IgG3           [shaded sequence]
IgG4           [shaded sequence]

IgG1m(1,17)    [shaded]GQPREPQVYTLPPSRDELTKNQVSLT
IgG1m(3)       [shaded]GQPREPQVYTLPPSREEMTKNQVSLT
IgG2           [shaded]GQPREPQVYTLPPCREEMTKNQVSLT
IgG3           [shaded]GQPREPQVYTLPPCREEMTKNQVSLT
IgG4           [shaded]GQPREPQVYTLPPQEEMTKNQVSLT IgG1m(1,17)    CLVKGFYPSDIAVEWESNGQPENNYKTTPPVLDSDGSFFLYSKLTVDKSRWQQGNVFSCSVMHEAL
IgG1m(3)       CLVKGFYPSDIAVEWESNGQPENNYKTTPPVLDSDGSFFLYSKLTVDKSRWQQGNVFSCSVMHEAL
IgG2           CLVKGFYPSDIAVEWESNGQPENNYKTTPPMLDSDGSFFLYSKLTVDKSRWQQGNVFSCSVMHEAL
IgG3           CLVKGFYPSDIAVEWESSGQPENNYNTTPPMLDSDGSFFLYSKLTVDKSRWQQGNIFSCSVMHEAL
IgG4           CLVKGFYPSDIAVEWESNGQPENNYKTTPPVLDSDGSFFLYSRLTVDKSRWQEGNVFSCSVMHEAL IgG1m(1,17)    HNHYTQKSLSLSPGK
IgG1m(3)       HNHYTQKSLSLSPGK
IgG2           HNHYTQKSLSLSPGK
IgG3           HNRFTQKSLSLSPGK
IgG4           HNHYTQKSLSLSLGK
```

Figure 1

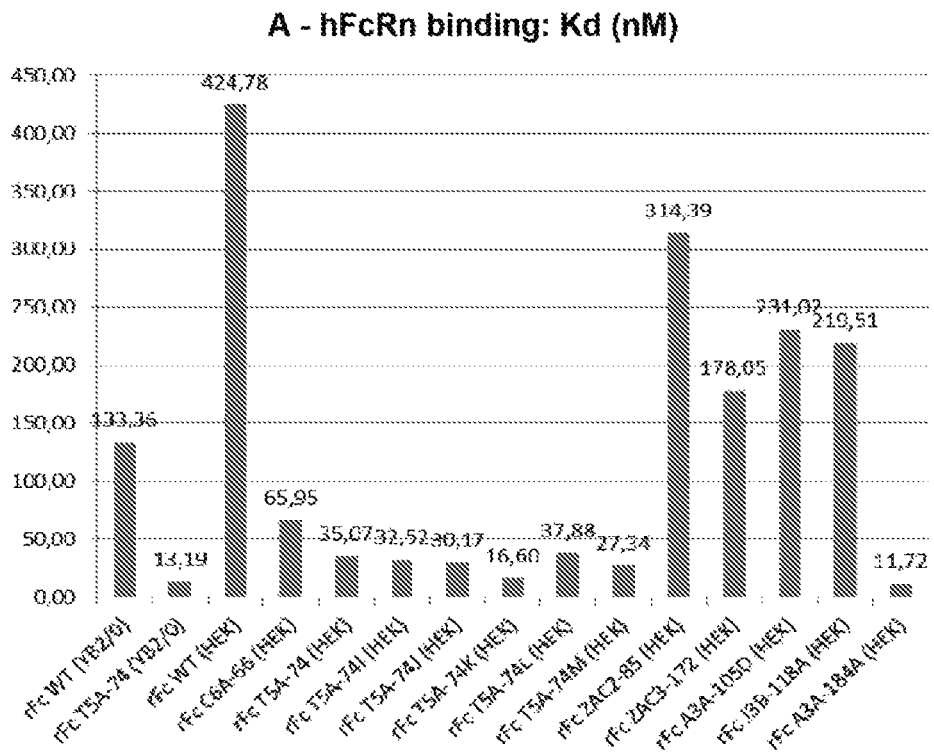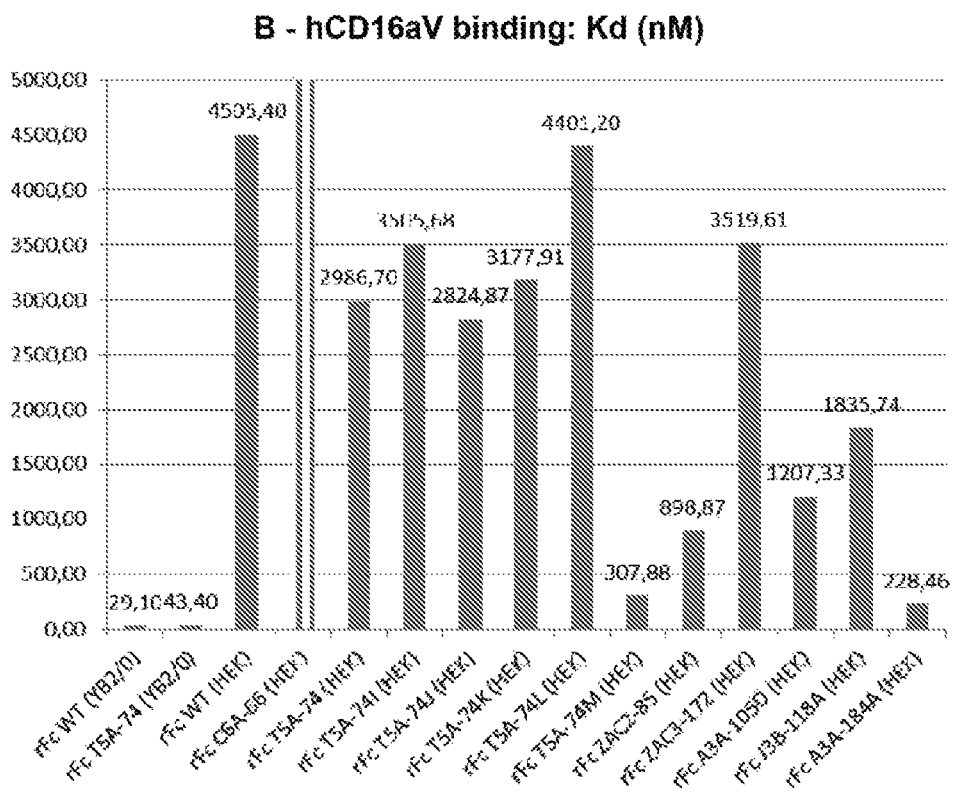
Figure 6

SEQUENCE LISTING

```
<160> NUMBER OF SEQ ID NOS: 21

<210> SEQ ID NO 1
<211> LENGTH: 222
<212> TYPE: PRT
<213> ORGANISM: Artificial Sequence
<220> FEATURE:
<223> OTHER INFORMATION: Fc of IgG1 G1m1,17

<400> SEQUENCE: 1

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 2
<211> LENGTH: 221
<212> TYPE: PRT
```

<213> ORGANISM: Artificial Sequence
<220> FEATURE:
<223> OTHER INFORMATION: Fc of IgG2

<400> SEQUENCE: 2

```
Cys Pro Pro Cys Pro Ala Pro Val Ala Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Gln
        35                  40                  45

Phe Asn Trp Tyr Val Asp Gly Val Glu Val His Asn Ala Lys Thr Lys
    50                  55                      60

Pro Arg Glu Glu Gln Phe Asn Ser Thr Phe Arg Val Val Ser Val Leu
65              70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
            100                 105                 110

Thr Lys Gly Gln Pro Arg Glu Pro Gln Val Tyr Thr Leu Pro Pro Ser
        115                 120                 125

Arg Glu Glu Met Thr Lys Asn Gln Val Ser Leu Thr Cys Leu Val Lys
130             135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Met Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220
```

<210> SEQ ID NO 3
<211> LENGTH: 222
<212> TYPE: PRT
<213> ORGANISM: Artificial Sequence
<220> FEATURE:
<223> OTHER INFORMATION: Fc of IgG3

<400> SEQUENCE: 3

```
Cys Pro Arg Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Lys Trp Tyr Val Asp Gly Val Glu Val His Asn Ala Lys Thr
    50                  55                  60

Lys Pro Arg Glu Glu Gln Tyr Asn Ser Thr Phe Arg Val Val Ser Val
65              70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110
```

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
        130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Ile Phe Ser Cys Ser Val Met His Glu Ala Leu His
            195                 200                 205

Asn Arg Phe Thr Gln Lys Ser Leu Ser Leu Ser Pro Gly Lys
        210                 215                 220

<210> SEQ ID NO 4
<211> LENGTH: 222
<212> TYPE: PRT
<213> ORGANISM: Artificial Sequence
<220> FEATURE:
<223> OTHER INFORMATION: Fc of IgG4

<400> SEQUENCE: 4

Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
                180                 185                 190

Gln Glu Gly Asn Val Phe Ser Cys Ser Val Met His Glu Ala Leu His
            195                 200                 205

Asn His Tyr Thr Gln Lys Ser Leu Ser Leu Ser Leu Gly Lys
        210                 215                 220

<210> SEQ ID NO 5
<211> LENGTH: 222
<212> TYPE: PRT
<213> ORGANISM: Artificial Sequence
<220> FEATURE:

<223> OTHER INFORMATION: Fc of IgG1 G1m3

<400> SEQUENCE: 5

```
Cys Pro Pro Cys Pro Ala Pro Glu Leu Leu Gly Gly Pro Ser Val Phe
1               5                   10                  15
Leu Phe Pro Pro Lys Pro Lys Asp Thr Leu Met Ile Ser Arg Thr Pro
            20                  25                  30
Glu Val Thr Cys Val Val Val Asp Val Ser His Glu Asp Pro Glu Val
        35                  40                  45
Lys Phe Asn Trp Tyr Val Asp Gly Val Glu Val His Asn Ala Lys Thr
    50                  55                  60
Lys Pro Arg Glu Glu Gln Tyr Asn Ser Thr Tyr Arg Val Val Ser Val
65                  70                  75                  80
Leu Thr Val Leu His Gln Asp Trp Leu Asn Gly Lys Glu Tyr Lys Cys
                85                  90                  95
Lys Val Ser Asn Lys Ala Leu Pro Ala Pro Ile Glu Lys Thr Ile Ser
            100                 105                 110
Lys Ala Lys Gly Gln Pro Arg Glu Pro Gln Val Tyr Thr Leu Pro Pro
        115                 120                 125
Ser Arg Glu Glu Met Thr Lys Asn Gln Val Ser Leu Thr Cys Leu Val
    130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Lys Leu Thr Val Asp Lys Ser Arg Trp
            180                 185                 190
Gln Gln Gly Asn Val Phe Ser Cys Ser Val Met His Glu Ala Leu His
        195                 200                 205
Asn His Tyr Thr Gln Lys Ser Leu Ser Leu Ser Pro Gly Lys
    210                 215                 220
```

<210> SEQ ID NO 6
<211> LENGTH: 232
<212> TYPE: PRT
<213> ORGANISM: Artificial Sequence
<220> FEATURE:
<223> OTHER INFORMATION: Fc of IgG1 G1m1,17

<400> SEQUENCE: 6

```
Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
```

```
Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 7
<211> LENGTH: 228
<212> TYPE: PRT
<213> ORGANISM: Artificial Sequence
<220> FEATURE:
<223> OTHER INFORMATION: Fc of IgG2

<400> SEQUENCE: 7

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 8
```

-continued

```
<211> LENGTH: 279
<212> TYPE: PRT
<213> ORGANISM: Artificial Sequence
<220> FEATURE:
<223> OTHER INFORMATION: Fc of IgG3

<400> SEQUENCE: 8

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 9
<211> LENGTH: 229
<212> TYPE: PRT
<213> ORGANISM: Artificial Sequence
<220> FEATURE:
<223> OTHER INFORMATION: Fc of IgG4

<400> SEQUENCE: 9

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
```

-continued

```
                35                  40                  45
Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 10
<211> LENGTH: 232
<212> TYPE: PRT
<213> ORGANISM: Artificial Sequence
<220> FEATURE:
<223> OTHER INFORMATION: Fc of IgG1 G1m3

<400> SEQUENCE: 10

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

165                 170                 175
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 11
<211> LENGTH: 227
<212> TYPE: PRT
<213> ORGANISM: Artificial Sequence
<220> FEATURE:
<223> OTHER INFORMATION: Fragment Fc mute T5A-74

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asp Gly
                85                  90                  95

Lys Glu Tyr Lys Cys Lys Val Ser Asn Lys Ala Leu Pro Val Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asp Gln Val Ser
    130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Tyr His Tyr Thr Gln Lys Ser Leu Ser Leu Ser
    210                 215                 220

Pro Gly Lys
225

<210> SEQ ID NO 12
<211> LENGTH: 227
<212> TYPE: PRT
<213> ORGANISM: Artificial Sequence
<220> FEATURE:
<223> OTHER INFORMATION: Fragment Fc mute T5A-74I

<400> SEQUENCE: 12

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Ala Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asp Gly
                85                  90                  95

Lys Glu Tyr Lys Cys Lys Val Ser Asn Lys Ala Leu Pro Val Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asp Gln Val Ser
            130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Tyr His Tyr Thr Gln Lys Ser Leu Ser Leu Ser
            210                 215                 220

Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: Fragment Fc mute T5A-74J

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Ile Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asp Gly
                85                  90                  95

Lys Glu Tyr Lys Cys Lys Val Ser Asn Lys Ala Leu Pro Val Pro Ile
            100                 105                 110

Glu Lys Thr Ile Ser Lys Ala Lys Gly Gln Pro Arg Glu Pro Gln Val
            115                 120                 125
```

```
Tyr Thr Leu Pro Pro Ser Arg Asp Glu Leu Thr Lys Asp Gln Val Ser
        130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Tyr His Tyr Thr Gln Lys Ser Leu Ser Leu Ser
210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: Fragment Fc mute T5A-74K

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Tyr Pro Arg Glu Glu Gln Tyr Asn Ser Thr Tyr
65                  70                  75                  80

Arg Val Val Ser Val Leu Thr Val Leu His Gln Asp Trp Leu Asp Gly
                85                  90                  95

Lys Glu Tyr Lys Cys Lys Val Ser Asn Lys Ala Leu Pro Val Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asp Gln Val Ser
        130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Tyr His Tyr Thr Gln Lys Ser Leu Ser Leu Ser
210                 215                 220

Pro Gly Lys
225

<210> SEQ ID NO 15
<211> LENGTH: 227
```

<212> TYPE: PRT
<213> ORGANISM: Artificial Sequence
<220> FEATURE:
<223> OTHER INFORMATION: Fragment Fc mute T5A-74L

<400> SEQUENCE: 15

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Ala Gln Tyr Asn Ser Thr Tyr
65                  70                  75                  80

Arg Val Val Ser Val Leu Thr Val Leu His Gln Asp Trp Leu Asp Gly
                85                  90                  95

Lys Glu Tyr Lys Cys Lys Val Ser Asn Lys Ala Leu Pro Val Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asp Gln Val Ser
    130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Tyr His Tyr Thr Gln Lys Ser Leu Ser Leu Ser
    210                 215                 220

Pro Gly Lys
225
```

<210> SEQ ID NO 16
<211> LENGTH: 227
<212> TYPE: PRT
<213> ORGANISM: Artificial Sequence
<220> FEATURE:
<223> OTHER INFORMATION: Fragment Fc mute T5A-74M

<400> SEQUENCE: 16

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Trp Asn Ser Thr Tyr
65                  70                  75                  80

Arg Val Val Ser Val Leu Thr Val Leu His Gln Asp Trp Leu Asp Gly
                85                  90                  95
```

```
Lys Glu Tyr Lys Cys Lys Val Ser Asn Lys Ala Leu Pro Val Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asp Gln Val Ser
        130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Tyr His Tyr Thr Gln Lys Ser Leu Ser Leu Ser
    210                 215                 220

Pro Gly Lys
225

<210> SEQ ID NO 17
<211> LENGTH: 227
<212> TYPE: PRT
<213> ORGANISM: Artificial Sequence
<220> FEATURE:
<223> OTHER INFORMATION: Fragment Fc mute ZAC2-85

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Ala Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 18
<211> LENGTH: 227
<212> TYPE: PRT
<213> ORGANISM: Artificial Sequence
<220> FEATURE:
<223> OTHER INFORMATION: Fragment Fc mute ZAC3-172

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Tyr Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 19
<211> LENGTH: 227
<212> TYPE: PRT
<213> ORGANISM: Artificial Sequence
<220> FEATURE:
<223> OTHER INFORMATION: Fragment Fc mute A3A-184A

<400> SEQUENCE: 19

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val

```
                 50                  55                  60
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Asn Thr Ile Ser Lys Ala Lys Gly Gln Pro Arg Glu Pro Gln Val
        115                 120                 125

Tyr Thr Leu Ser Pro Ser Arg Asp Glu Leu Thr Lys Asn Gln Val Ser
    130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 20
<211> LENGTH: 227
<212> TYPE: PRT
<213> ORGANISM: Artificial Sequence
<220> FEATURE:
<223> OTHER INFORMATION: Fragment Fc mute A3A-105D

<400> SEQUENCE: 20

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Asp
                 85                  90                  95

Lys Glu Tyr Lys Cys Lys Val Ser Asn Glu Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Val Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
```

-continued

```
                      180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro Gly Lys
225

<210> SEQ ID NO 21
<211> LENGTH: 227
<212> TYPE: PRT
<213> ORGANISM: Artificial Sequence
<220> FEATURE:
<223> OTHER INFORMATION: Fragment Fc mute J3B-118A

<400> SEQUENCE: 21

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Val Val Glu
145                 150                 155                 160
Trp Glu Ser Asn Gly Gln Pro Glu Asn Asn Tyr Lys Thr Thr Pro Leu
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Thr Val Phe Ser Cys Ser Val Met
            195                 200                 205
His Glu Ala Leu His Asn His Tyr Thr Gln Lys Ser Leu Ser Leu Ser
            210                 215                 220
Pro Gly Lys
225
```

USE OF MODIFIED Fc FRAGMENTS IN IMMUNOTHERAPY

RELATED APPLICATIONS

This application is a national stage filing under 35 U.S.C. § 371 of International Application No. PCT/FR2016/051708, filed Jul. 6, 2016, which claims priority to French Application No. 1556399, filed Jul. 6, 2015, the entire contents of each of which is incorporated herein by reference in its entirety.

The present invention relates to immunotherapy of autoimmune and/or inflammatory diseases.

BACKGROUND OF THE INVENTION

Immunotherapy, which consists of administering exogenous antibodies to patients, is widely used today for the treatment of various pathologies, particularly for that of autoimmune diseases and inflammatory diseases.

Two types of immunoglobulin-based therapy are typically proposed for the treatment of these diseases: i) therapies based on intravenous immunoglobulins (IVIg), consisting of intravenous administration of immunoglobulins (most often IgG) derived from human plasma pools to patients and ii) therapies based on the use of recombinant antibodies (namely antibodies obtained by genetic engineering). The later have enabled genuine advances in the management of patients with inflammatory diseases and autoimmune diseases, notably because they offer the possibility of avoiding the disadvantages associated with the use of immunoglobulins from plasma, especially the risk of supply shortages, and the risk of transmission of pathogens potentially present in plasma.

The presence of Fab fragments in immunoglobulins may be responsible for significant adverse reactions in treated patients. To avoid these side effects, patent application WO 2004/099374 discloses the use of isolated recombinant Fc fragments for the treatment of patients, in particular for patients with autoimmune disease.

There remains a need to optimize these Fc fragments, however, so as in particular to increase their half-life and/or therapeutic efficacy.

SUMMARY OF THE INVENTION

The inventors now propose to use Fc fragments having a modified affinity for at least one Fc receptor (FcR) in comparison with a parent Fc fragment. According to the invention, the Fc fragments are isolated, i.e., they are not associated with Fab fragments or conjugated or fused to any other protein, polypeptide or peptide. In particular, they are not complete immunoglobulins.

The invention relates to a composition comprising antibody Fc fragments, for use in the treatment of an autoimmune and/or inflammatory disease, said Fc fragments being isolated Fc fragments having an improved affinity for Fc-gamma receptor III (FcγRIII) in comparison with a parent Fc fragment.

In preferred aspects, they are

Fc fragments having a combination of mutations 315D/330V/361D/378V/434Y in comparison with a parent Fc fragment of wild-type IgG1, preferably wherein the Fc fragments consist of sequence SEQ ID NO: 11

Fc fragments having a combination of mutations T260A and 315D/330V/361D/378V/434Y in comparison with a parent Fc fragment of wild-type IgG1, preferably wherein the Fc fragments consist of sequence SEQ ID NO: 12

Fc fragments having a combination of mutations E258I and 315D/330V/361D/378V/434Y in comparison with a parent Fc fragment of wild-type IgG1, preferably wherein the Fc fragments consist of sequence SEQ ID NO: 13

Fc fragments having a combination of mutations K290Y and 315D/330V/361D/378V/434Y in comparison with a parent Fc fragment of wild-type IgG1, preferably wherein the Fc fragments consist of sequence SEQ ID NO: 14

Fc fragments having a combination of mutations E294A and 315D/330V/361D/378V/434Y in comparison with a parent Fc fragment of wild-type IgG1, preferably wherein the Fc fragments consist of sequence SEQ ID NO: 15

Fc fragments having a combination of mutations Y296W and 315D/330V/361D/378V/434Y in comparison with a parent Fc fragment of wild-type IgG1, preferably wherein the Fc fragments consist of sequence SEQ ID NO: 16

Fc fragments having a combination of mutations K334N/P352S/A378V/V397M in comparison with a parent Fc fragment of wild-type IgG1, preferably wherein the Fc fragments consist of sequence SEQ ID NO: 19

Fc fragments having a combination of mutations G316D/K326E/A378V in comparison with a parent Fc fragment of wild-type IgG1, preferably wherein the Fc fragments consist of sequence SEQ ID NO: 20

Fc fragments having a combination of mutations A378V/P396L/N421T in comparison with a parent Fc fragment of wild-type IgG1, preferably wherein the Fc fragments consist of sequence SEQ ID NO: 21

Fc fragments having a mutation T260A in comparison with a parent Fc fragment of wild-type IgG1, preferably wherein the Fc fragments consist of sequence SEQ ID NO: 17

Fc fragments having a mutation K290Y in comparison with a parent Fc fragment of wild-type IgG1, preferably wherein the Fc fragments consist of sequence SEQ ID NO: 18.

The invention also more generally provides a composition comprising antibody Fc fragments, for use in the treatment of an autoimmune and/or inflammatory disease, said Fc fragments being isolated Fc fragments having modified affinity for at least one Fc receptor (FcR) in comparison with a parent Fc fragment.

In a particular embodiment, the composition comprises antibody Fc fragments, having at least one mutation of one or more amino acids and/or having N-glycans on the glycosylation site (Asn 297) thereof, said N-glycans of the Fc fragments having a degree of fucosylation lower than 65%.

BRIEF DESCRIPTION OF THE FIGURES

FIG. 1 shows sequence alignments of native human IgG1 with regard to positions 216 to 447 (according to the EU index) with the corresponding sequences of human IgG2 (SEQ ID NO: 7), human IgG3 (SEQ ID NO: 8) and human IgG4 (SEQ ID NO: 9). The IgG1 sequences refer to the G1m1,17 allotype (SEQ ID NO: 6) and to the G1m3 allotype (SEQ ID NO: 10). The "CH2-CH3 lower hinge" domain of IgG1 begins at position 226 (see arrow). The CH2 domain is highlighted in gray and the CH3 domain is in italics.

FIG. 6 represents an in vitro binding assay measuring the affinity (Kd) of WT (wild-type) and mutated Fc fragments for human FcRn (A) and for CD16aV (V polymorphism at position 158 of CD16) (B), evaluated by surface plasmon resonance (SPR) using Biacore.

DETAILED DESCRIPTION OF THE INVENTION

Definitions

Figure 2:
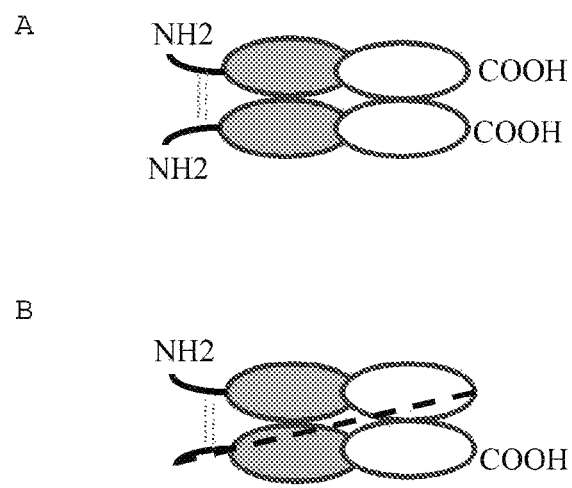
FIG. 2 shows schematic representations of IgG1 Fc (A) and an scFc (B). The CH2 are represented in gray and the CH3 in white. Disulfide bridges are represented by thin gray dotted lines. In the scFc, the two CH2-CH3 polypeptides are connected by a peptide linker represented by bold dotted lines.

Throughout the present description, the numbering of the residues in the Fc fragment is that of the immunoglobulin heavy-chain according to the EU index or as described in Kabat et al., Sequences of proteins of immunological interest, $5^{th}$ Ed. Public Health Service, National Institutes of Health, Bethesda, Md. (1991), expressly incorporated by reference herein. "EU index" or "EU index or the Kabat equivalent" refers herein to the numbering of the residues of human IgG1 antibody.

The term "immunoglobulin" refers to the structure constituting the natural-state biological form of an antibody, including the constant and variable regions (also called fragments). An immunoglobulin molecule is a molecule whose basic unit is a heterotetramer consisting of two heavy (H) chains of roughly 50-70 kDa each and two light (L) chains of roughly 25 kDa each, bound together by intra- and intercatenary disulfide bridges.

Each chain is composed, in the N-terminal position, of a variable domain or region, called VL in the case of the light chain and VH in the case of the heavy chain; and in the C-terminal position, of a constant region consisting of a single domain called CL in the case of the light chain and of three or four domains called CH1, CH2, CH3 and CH4 in the case of the heavy chain.

Only IgM and IgE have the CH4 domain.

Each domain comprises about 110 amino acids and is structured in a comparable manner. The two heavy chains are linked by disulfide bridges at the CH2 domains and each heavy chain is linked to a light chain by a disulfide bridge between CH1 and CL. The region that determines the antibody's specificity for the antigen is carried by the variable portions, whereas the constant portions can interact with the Fc receptors (FcR) of effector cells or molecules such as complement proteins in order to induce various functional properties. The assembly of the chains composing an antibody makes it possible to define a characteristic Y-shaped three-dimensional structure, where
    the base of the Y corresponds to the constant Fc region (or Fc fragment) which is recognized by the complement and Fc receptors in order to mediate the effector functions of the molecule, and
    the ends of the arms of the Y correspond to the respective assembly of a light chain variable region and a heavy chain variable region, said ends constituting the Fab fragment and determining the antibody's specificity for the antigen.

More precisely, there are five heavy chain isotypes (gamma, alpha, mu, delta and epsilon) and two light chain isotypes (kappa and lambda, the lambda chains themselves being divided into two types: lambda 1 and lambda 2). It is the heavy chain which determines the immunoglobulin class. There are thus five classes of Ig: IgG (gamma isotype), IgA (alpha isotype), IgM (mu isotype), IgD (delta isotype) and IgE (epsilon isotype).

The kappa and lambda light chains are shared by all the classes and subclasses. In humans, the proportion of kappa and lambda produced is in a ratio of 2 to 1.

IgG are the most abundant immunoglobulins in serum (75% to 80% of circulating antibodies). Present in monomer form, they have the longest serum half-life of all the immunoglobulins (about 21 days).

There are four types of gamma heavy chains, which determine the four IgG subclasses (IgG1 for gamma 1, IgG2 for gamma 2, IgG3 for gamma 3 and IgG4 for gamma 4). These four subclasses differ in terms of variable numbers and positions of disulfide bridges (Basic and Clinical Immunology, $8^{th}$ Edition, Daniel P. Stites, Abba I. Terr and Tristram G. Parslow (eds.), Appleton & Lange, Norwalk, Conn., 1994, page 71 and Chapter 6).

The four human IgG subclasses are also distinguished by their biological activities, despite highly homologous structures (more than 95% sequence homology for the Fc regions).

The term "biological activity" notably refers to the capacity of the IgG constant region to bind to complement proteins in particular (protein C1q for example [Basic and Clinical Immunology, $8^{th}$ Edition, Daniel P. Stites, Abba I. Terr and Tristram G. Parslow (eds.)]) and/or to IgG receptors: FcγR (FcγRI, FcγRII, FcγRIII; Ravetch and Kinet, Annual Review of Immunology, Vol. 9:457-492 (1991)).

Depending on the type of binding, various action mechanisms may be activated: opsonization, phagocytosis, antibody-dependent cellular cytotoxicity (ADCC) or complement-dependent cytotoxicity (CDC), for example. See Uananue and Benacerraf, Textbook of Immunology, $2^{nd}$ Edition, Williams & Wilkins, p. 218 (1984)) for further details.

The term "Fc fragment" refers to the constant region of a full-length immunoglobulin excluding the first immunoglobulin constant region domain. Thus, "Fc fragment" refers to the last two constant domains (CH2-CH3) of IgA, IgD, IgG and the last three constant domains (CH2-CH3-CH4) of IgE and IgM, and the N-terminal flexible hinge of these domains. For IgA and IgM, the Fc fragment may comprise the J chain. For IgG, the Fc fragment comprises the CH2, CH3 domains and the lower hinge region between CH1 and CH2. In other words, the Fc region of an IgG1 is composed of the CH2-CH3 lower hinge, i.e., the portion from amino acid C226 to the carboxy-terminal end, the numbering being indicated according to the EU index or the Kabat equivalent. The analogous domains for other IgG subclasses can be determined from the alignment of the amino acid sequences of the heavy chains or the heavy chain fragments of the IgG subclasses with that of human IgG1 (see FIG. 1). The Fc fragment used according to the invention may further comprise a portion of the upper hinge region, upstream of position 226 (according to the EU index). In this case, preferably, use is made of an Fc fragment of a human IgG1 comprising a portion of the region located between positions 216 and 226. In this case, "Fc fragment of a human IgG1" refers to the portion from amino acid 216, 217, 218, 219, 220, 221, 222, 223, 224 or 225 to the carboxy-terminal end. The term "Fc fragment" also refers to a single-chain Fc (scFc) fragment. The term "scFc fragment" refers to a single-chain Fc fragment, obtained by genetic fusion of two Fc monomers connected by a polypeptide linker. The scFc folds naturally into a functional dimeric Fc region.

The term "parent Fc fragment" or "parent polypeptide" as used herein refers to a reference polypeptide among the wild-type Fc regions or variants optionally containing mutations other than that considered. The term "wild-type" or "WY" refers herein to an amino acid sequence or a nucleotide sequence which is found in nature i.e., which is of natural origin, including allelic variations, and which has not been modified intentionally by molecular biology techniques such as mutagenesis. For example, "wild-type" Fc regions notably refer to the IgG1 Fc region with sequence SEQ ID NO: 1 (G1m1,17 allotype), the IgG2 Fc region with sequence SEQ ID NO: 2, the IgG3 Fc region with sequence SEQ ID NO: 3, the IgG4 Fc region with sequence SEQ ID NO: 4, and the IgG1 Fc region with sequence SEQ ID NO: 5 (G1m3 allotype).

The Fc fragments used in the invention are in monomeric form, i.e., they are not fused or conjugated to each other.

The term "modified affinity" refers to a decreased or increased affinity in comparison with a parent Fc fragment.

The term "neonatal Fc receptor" or "FcRn" as used herein refers to a protein which binds to the IgG Fc region and is encoded at least in part by an FcRn gene. The FcRn may be from any organism, including but not limited to humans, mice, rats, rabbits and monkeys. As known in the state of the art, the functional FcRn protein comprises two polypeptides, often designated by the name of the heavy chain and of the light chain. The light chain is β2-microglobulin and the heavy chain is encoded by the FcRn gene. Unless otherwise specified herein, the term "FcRn" or "FcRn protein" refers to the complex of the α chain with β2-microglobulin. In humans, the gene encoding FcRn is called FCGRT.

The term "increase in FcRn binding" as used herein refers to the increase in the binding affinity, in vivo or in vitro, of the mutated Fc fragment of the invention for FcRn, in comparison with the parent polypeptide. The capacity of the mutated Fc fragment of the invention to bind to an FcRn can be evaluated in vitro by ELISA, as described for example in patent application WO2010/106180.

In the present invention, the term "half-life" refers to the amount of time for the Fc fragment to be eliminated by half from the circulation or from other tissues, once present in the serum of the patient to which it has been administered.

The term "Fcγ receptor" or "FcγR" refers to IgG-type immunoglobulin receptors, called CD64 (FcγRI), CD32 (FcγRII) and CD16 (FcγRIII), in particular five expressed receptors (FcγRIa, FcγRIIa, FcγRIIb, FcγRIIIa, FcγRIIIb). All are effector cell-activating receptors, except for human FcγRIIb, which is a receptor that inhibits immune cell activation (Muta T et al., Nature, 1994, 368:70-73).

The term "effector cell" refers to any cell bearing an Fc receptor, such as lymphocytes, monocytes, neutrophils, natural killer (NK) cells, eosinophils, basophils, mastocytes, dendritic cells, Langerhans cells and platelets.

In the context of the invention, the term "glycosylation" refers to the addition, by enzymatic reaction, of one or more carbohydrates to the sequence of a recombinant Fc fragment.

In the context of the invention, the term "hypersialylation" refers to the addition of one or more sialic acid groups to the sequence of an Fc fragment. The addition of one or more sialic acid groups may be carried out by enzymatic reaction, by cellular reaction or by directed mutagenesis of the Fc targeting one or more amino acids involved in Fc sialylation.

The term "patient" refers to any human or animal subject, preferably mammalian. In a preferred embodiment, the patient is a human being, regardless of age and sex.

The term "treatment" or "treat" refers to an improvement in or the prophylaxis or the reversal of a disease or a disorder, or at least a symptom which can be distinguished therefrom, or an improvement in or the prophylaxis or reversal of at least one measurable physical parameter associated with the disease or the disorder being treated, which is not necessarily distinguishable in or by the treated subject. The term "treatment" or "treat" further includes the inhibition or slowing down of the progression of a disease or a disorder, physically, for example, the stabilization of a distinguishable symptom, physiologically, for example, the stabilization of a physical parameter, or both.

Compositions of Fc Fragments According to the Invention

The antibody Fc fragments used in the invention are preferably Fc fragments of an IgG1, IgG2, IgG3 or IgG4 immunoglobulin, having a modified affinity for at least one Fc receptor (FcR) in comparison with a parent Fc fragment.

The Fc fragments according to the invention have a decreased affinity for at least one Fc receptor and/or an increased affinity for at least one Fc receptor, in comparison with a parent Fc fragment.

Preferentially, the affinity is increased, in comparison with that of the parent Fc, by a ratio at least equal to 2, preferably higher than 5, preferably higher than 10, preferably higher than 15, preferably higher than 20, preferably higher than 25, and preferably higher than 30. In other words, the affinity of the mutated Fc region for an FcR is higher than that of the parent polypeptide. Alternatively, said mutated Fc region has a decreased affinity for at least one FcR. Preferentially, the affinity is decreased, in comparison with that of the parent Fc, by a ratio at least equal to 2, preferably higher than 5, preferably higher than 10, preferably higher than 15, preferably higher than 20, preferably higher than 25, and preferably higher than 30. In other words, the affinity of the mutated Fc region for an FcR is lower than that of the parent polypeptide.

The affinity of a polypeptide comprising an Fc region for an FcR may be evaluated by methods well-known in the prior art. For example, the person skilled in the art may determine the affinity (Kd) by using surface plasmon resonance (SPR), which can be measured by the Biacore system. Alternatively, the person skilled in the art may perform a suitable ELISA. A suitable ELISA can be used to compare the binding forces of the parent Fc and of the mutated Fc. The specific signals detected from the mutated Fc and from the parent Fc are compared. The binding affinity may be equally determined by evaluating the entire polypeptides or by evaluating the Fc regions isolated therefrom.

In particular, the Fc fragments used according to the invention have a decreased affinity for at least one Fc receptor selected from FcRn, an Fcγ receptor, and complement C1q, and/or an increased affinity for at least one Fc receptor selected from FcRN, an Fcγ receptor, and complement C1q, in comparison with a parent Fc fragment.

According to a particular embodiment, the Fc fragments used according to the invention have a modified affinity, advantageously an increased affinity, for FcRn. This increase in FcRn binding results in an improvement in serum retention in vivo and, consequently, an increase in half-life.

The Fc fragments may be used alone or in mixture; for example, several Fc fragments having different mutations may be administered in a mixture or co-administered.

The Fc fragments of the invention may also be used in a composition comprising a single type of mutated Fc fragment. In other words, the composition comprises molecules of Fc fragments of identical sequence.

According to an aspect of the invention, the Fc fragments having a modified affinity for at least one Fc receptor contain a mutation of at least one amino acid in comparison with a parent Fc fragment. The mutations concerned are not the natural variations that define the immunoglobulin isotype, but artificial mutations, the production process generating the Fc fragment containing the desired mutation(s).

Preferably, the mutation is a substitution, a deletion or an insertion of one or more amino acids. The mutated Fc fragments may have several mutations, affecting several amino acids, preferably from two to ten.

In a preferred embodiment, the Fc fragments have a mutation selected from the group consisting of a mutation at amino acid 226, 227, 228, 230, 231, 233, 234, 239, 241, 243, 246, 250, 252, 256, 259, 264, 265, 267, 269, 270, 276, 284, 285, 288, 289, 290, 291, 292, 293, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 or 447, the numbering of the Fc fragment amino acids referring to that of the EU index or the Kabat equivalent.

Certain amino acid positions from the list above—namely 226, 230, 241, 256, 259, 264, 307, 315, 330, 342, 361, 362, 378, 382, 383, 389, 396, 397, 421, 428 and 434—are preferred. In particular, the mutated Fc fragments which have a high binding affinity for FcRn may comprise at least one amino acid change at said amino acid positions. Among these, positions 230, 264, 307, 315, 330, 378 and 434 are preferred, more preferably positions 264, 315, 378 and 434.

In a particular embodiment, at least two, indeed three, four or five amino acid mutations may substantially improve the binding affinity for FcRn in comparison with the parent Fc.

In a particular embodiment, the mutations are:
(i) one or two mutations selected from the group consisting of positions 226, 230, 241, 264, 307, 315, 330, 342, 362, 378, 382, 389, 396, 397, 421 and 434; preferably 230, 264, 307, 315, 330, 378 and 434, more preferably 264, 315, 378 and 434; and
(ii) at least one other, different mutation selected from positions 226, 227, 228, 230, 231, 233, 234, 239, 241, 243, 246, 250, 252, 256, 259, 264, 265, 267, 269, 270, 276, 284, 285, 288, 289, 290, 291, 292, 293, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447, preferably 226, 230, 241, 264, 307, 315, 330, 342, 362, 378, 382, 389, 396, 397, 421 and 434.

In a preferred embodiment, at least one of positions 378 and 434 is mutated; and optionally also at least one other selected from the group consisting of 226, 230, 241, 264, 307, 315, 330, 342, 362, 378, 382, 389, 396, 397, 421 and 434.

Preferably, the mutations are 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 289I, 290R, 290E, 291S, 291Q, 292W, 293del, 294del, 297D, 298G, 298N, 299M, 299A, 299K, 301C, 302A, 303A, 303I, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447N and 447E, and are also described in patent application WO2010/106180.

In another embodiment, the Fc fragments comprise at least one mutation selected from the group consisting of 226G, 227L, 230S, 230T, 230L, 231T, 241L, 243L, 250A, 256N, 259I, 264E, 265G, 267R, 290E, 293del, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R, preferably 226G, 230S, 230T, 230L, 241L, 264E, 307P, 315D, 330V, 342R, 362R, 362E, 378V, 378T, 382V, 389T, 389K, 396L, 397M, 421T, 434Y and 434S.

Examples of particular combinations of mutations are presented below:
226G/330V, 230L/264E, 230L/378V, 230S/315D, 230S/434Y, 230T/378V, 241L/434S, 250A/434Y, 264E/378T, 305A/315D, 305A/330V, 305A/434Y, 307P/434Y, 315D/389T, 330V/382G, 330V/389T, 378V/421T, 389K/434Y, 389T/434Y, 396L/434S, 230T/264E, 230T/315D, 230T/434S, 230T/434Y, 241L/

307P, 264E/307P, 264E/396L, 315D/362R, 315D/
382V, 362R/434Y, 378V/434Y, 382V/434Y, 226G/
315D, 226G/434Y, 241L/378V, 307P/378V, 241L/
264E, 378V/434S, 264E/378V, 264E/434S, 315D/
330V, 330V/434Y and 315D/434Y; or
226G/315D/330V, 226G/315D/434Y, 226G/330V/434Y,
230L/264E/378V, 230T/264E/378V, 230T/264E/434S,
230S/315D/434Y, 230T/315D/434Y, 230T/389T/434S,
241L/264E/434S, 241L/264E/378V, 241L/264E/307P,
241L/307P/378V, 250A/389K/434Y, 256N/378V/
434Y, 259I/315D/434Y, 264E/378T/396L, 264E/378V/
416K, 294del/307P/434Y, 264E/307P/378V, 264E/
396L/434S, 264E/378V/434S, 305A/315D/330V,
305A/315D/434Y, 305A/330V/434Y, 307P/378V/
434Y, 315D/330V/382V, 315D/330V/389T, 315D/
378V/434Y, 315D/389T/434Y, 315D/362R/434Y,
315D/382V/434Y, 315D/330V/434Y, 330V/382V/
434Y, 330V/389T/434Y and 378V/383N/434Y.

In a particularly advantageous embodiment, the Fc fragments have a combination of mutations selected from 315D/330V/361D/378V/434Y (combination of mutations also called "T5A-74"; Fc fragments with this combination of mutations are thus also called "rFc T5A-74"), 230S/315D/428L/434Y, 307A/315D/330V/382V/389T/434Y, 259I/315D/434Y, 256N/378V/383N/434Y, E294del/T307P/N434Y (combination of mutations also called "C6A_66"; Fc fragments with this combination of mutations are thus also called "rFc C6A_66").

In another embodiment, the Fc fragments have at least one mutation selected from V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of said Fc fragment; the numbering being that of the EU index or the Kabat equivalent.

In an embodiment, the variant according to the invention has an increased affinity for FcγRIIIa (CD16a). In this particular embodiment, said variant comprises at least one mutation i) selected from S298A, S298R, F243S, F243L, L242A, L242F, L242G, L242I, L242K, L242S, L242V, V240I, V240M, V240N, V240S, E258I, T260A, K290D, K290E, K290G, K290H, K290Q, K290S, K290Y, Y296H, Y296W of said Fc fragment;
the numbering being that of the EU index or the Kabat equivalent.

Particular Fc fragments are fragments ZAC2-85 (T260A), of sequence SEQ ID NO: 17:

DKTHTCPPCPAPELLGGPSVFLFPPKPKDTLMISRTPEVACVVVDVSH

EDPEVKFNWYVDGVEVHNAKTKPREEQYNSTYRVVSVLTVLHQDWLNG

-continued
KEYKCKVSNKALPAPIEKTISKAKGQPREPQVYTLPPSRDELTKNQVS

LTCLVKGFYPSDIAVEWESNGQPENNYKTTPPVLDSDGSFFLYSKLTV

DKSRWQQGNVFSCSVMHEALHNHYTQKSLSLSPGK

Or ZAC3-172 (K290Y), of sequence SEQ ID NO: 18:

DKTHTCPPCPAPELLGGPSVFLFPPKPKDTLMISRTPEVTCVVVDVSH

EDPEVKFNWYVDGVEVHNAKTYPREEQYNSTYRVVSVLTVLHQDWLNG

KEYKCKVSNKALPAPIEKTISKAKGQPREPQVYTLPPSRDELTKNQVS

LTCLVKGFYPSDIAVEWESNGQPENNYKTTPPVLDSDGSFFLYSKLTV

DKSRWQQGNVFSCSVMHEALHNHYTQKSLSLSPGK

In another embodiment, the variant according to the invention has an increased affinity for FcγRIIa (CD32a). In this particular embodiment, said variant comprises at least one mutation i) selected from F241H, F241Y, F243L, L242A, L242F, L242G, L242H, L242I, L242K, L242P, L242S, L242T, L242V, V240H, V240I, V240M, V240S, E258G, E258I, E258R, E258M, E258Q, E258Y, S267A, S267Q, S267V, T260A, T260H, T260I, T260M, T260N, T260R, T260S, T260W, V259C, V259I, V259L, V262A, V262S, V263T, V264L, V264S, V264T, V266L, V266M, E293A, E293D, E293G, E293M, E293Q, E293S, E293T, E294A, E294G, E294P, E294Q, E294R, E294T, E294V, K290D, K290E, K290G, K290H, K290L, K290N, K290Q, K290R, K290S, K290Y, P291G, P291Q, P291R, Q295I, Q295M, R292I, R292L, R301A, R301P, R301S, S304T, V302A, V302F, V302L, V302M, V302R, V302S, V303Y, V305A, V305F, V305L, V305R, V305S, Y300I, Y300V or Y300W; the numbering being that of the EU index or the Kabat equivalent.

In another embodiment, the variant according to the invention has an increased affinity for FcγRIIb (CD32b). In this particular embodiment, said variant comprises at least one mutation i) selected from E258R, E258Y, V262A, S267A, S267Q, S267V, V264S, V266L, V266M, K290R, R301A, R301M, S304T, V302A, V302L, V302R, V303S, V305A, V305F, V305I, V305R, Y300V of said Fc fragment; the numbering being that of the EU index or the Kabat equivalent.

Preferably, the variant according to the invention is characterized in that the Fc fragment of the parent polypeptide comprises at least:
(i) V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of said Fc fragment; the numbering being that of the EU index or the Kabat equivalent.

(ii) at least one mutation selected from 226G, P228L, P228R, 230S, 230T, 230L, 241L, 264E, 307P, 315D, 330V, 361D, 362R, 378V, 378T, 389T, 389K, 434Y and 434S, the numbering being that of the EU index or the Kabat equivalent and with the condition that mutations (ii) and (iii) are not on the same amino acids.

In a particularly advantageous embodiment, the Fc fragments have a combination of mutations selected from:
(i) T260A and 315D/330V/361D/378V/434Y (combination of mutations also called "T5A-74"). The fragment designated "T5A-74I" is an Fc fragment which is distinguished from fragment T5A-74 only by the addition of mutation T260A.

Or (ii) E258I and 315D/330V/361D/378V/434Y (combination of mutations also called "T5A-74"). The fragment designated "T5A-74J" is an Fc fragment which is distinguished from fragment T5A-74 only by the addition of mutation E258I.

Or (iii) K290Y and 315D/330V/361D/378V/434Y (combination of mutations also called "T5A-74"). The fragment designated "T5A-74K" is an Fc fragment which is distinguished from fragment T5A-74 only by the addition of mutation K290Y.

Or (iv) E294A and 315D/330V/361D/378V/434Y (combination of mutations also called "T5A-74"). The fragment designated "T5A-74L" is an Fc fragment which is distinguished from fragment T5A-74 only by the addition of mutation E294A.

Or (v) Y296W and 315D/330V/361D/378V/434Y (combination of mutations also called "T5A-74"). The fragment designated "T5A-74M" is an Fc fragment which is distinguished from fragment T5A-74 only by the addition of mutation Y296W.

The sequences of Fc fragments T5A-74, T5A-74I, T5A-74J, T5A-74K, T5A-74L, T5A-74M are presented in the attached sequence listing.

```
T5A-74 (N315D/A330V/N361D/A378V/N434Y):
                                         SEQ ID NO: 11
DKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLDG
KEYKCKVSNKALPVPIEKTISKAKGQPREPQVYTLPPSRDELTKDQVS
LTCLVKGFYPSDIVVEWESNGQPENNYKTTPPVLDSDGSFFLYSKLTV
DKSRWQQGNVFSCSVMHEALHYYTQKSLSLSPGK

T5A-74I (T260A/N315D/A330V/N361D/A378V/N434Y)
                                         SEQ ID NO: 12
DKTHTCPPCPAPELLGGPSVFLFPPKPKDTLMISRTPEVACVVVDVSH
EDPEVKFNWYVDGVEVHNAKTKPREEQYNSTYRVVSVLTVLHQDWLDG
KEYKCKVSNKALPVPIEKTISKAKGQPREPQVYTLPPSRDELTKDQVS
LTCLVKGFYPSDIVVEWESNGQPENNYKTTPPVLDSDGSFFLYSKLTV
DKSRWQQGNVFSCSVMHEALHYYTQKSLSLSPGK

T5A-74J (E258I/N315D/A330V/N361D/A378V/N434Y)
                                         SEQ ID NO: 13
DKTHTCPPCPAPELLGGPSVFLFPPKPKDTLMISRTPIVTCVVVDVSH
EDPEVKFNWYVDGVEVHNAKTKPREEQYNSTYRVVSVLTVLHQDWLDG
KEYKCKVSNKALPVPIEKTISKAKGQPREPQVYTLPPSRDELTKDQVS
LTCLVKGFYPSDIVVEWESNGQPENNYKTTPPVLDSDGSFFLYSKLTV
DKSRWQQGNVFSCSVMHEALHYYTQKSLSLSPGK

T5A-74K (K290Y/N315D/A330V/N361D/A378V/N434Y)
                                         SEQ ID NO: 14
DKTHTCPPCPAPELLGGPSVFLFPPKPKDTLMISRTPEVTCVVVDVSH
EDPEVKFNWYVDGVEVHNAKTYPREEQYNSTYRVVSVLTVLHQDWLDG
KEYKCKVSNKALPVPIEKTISKAKGQPREPQVYTLPPSRDELTKDQVS
LTCLVKGFYPSDIVVEWESNGQPENNYKTTPPVLDSDGSFFLYSKLTV
DKSRWQQGNVFSCSVMHEALHYYTQKSLSLSPGK

T5A-74L (E294A/N315D/A330V/N361D/A378V/N434Y)
                                         SEQ ID NO: 15
DKTHTCPPCPAPELLGGPSVFLFPPKPKDTLMISRTPEVTCVVVDVSH
EDPEVKFNWYVDGVEVHNAKTKPREAQYNSTYRVVSVLTVLHQDWLDG
KEYKCKVSNKALPVPIEKTISKAKGQPREPQVYTLPPSRDELTKDQVS
LTCLVKGFYPSDIVVEWESNGQPENNYKTTPPVLDSDGSFFLYSKLTV
DKSRWQQGNVFSCSVMHEALHYYTQKSLSLSPGK

T5A-74M (Y296W/N315D/A330V/N361D/A378V/N434Y)
                                         SEQ ID NO: 16
DKTHTCPPCPAPELLGGPSVFLFPPKPKDTLMISRTPEVTCVVVDVSH
EDPEVKFNWYVDGVEVHNAKTKPREEQWNSTYRVVSVLTVLHQDWLDG
KEYKCKVSNKALPVPIEKTISKAKGQPREPQVYTLPPSRDELTKDQVS
LTCLVKGFYPSDIVVEWESNGQPENNYKTTPPVLDSDGSFFLYSKLTV
DKSRWQQGNVFSCSVMHEALHYYTQKSLSLSPGK
```

Preferably, the variant according to the invention is characterized in that the Fc fragment of the parent polypeptide comprises at least:
(i) V240H, V240I, V240M, V240N, V240S, F241H, F241Y, L242A, L242F, L242G, L242H, L242I, L242K, L242P, L242S, L242T, L242V, F243L, F243S, E258G, E258I, E258R, E258M, E258Q, E258Y, V259C, V259I, V259L, T260A, T260H, T260I, T260M, T260N, T260R, T260S, T260W, V262A, V262S, V263T, V264L, V264S, V264T, V266L, V266M, S267A, S267Q, S267V, K290D, K290E, K290G, K290H, K290L, K290N, K290Q, K290R, K290S, K290Y, P291G, P291Q, P291R, R292I, R292L, E293A, E293D, E293G, E293M, E293Q, E293S, E293T, E294A, E294G, E294P, E294Q, E294R, E294T, E294V, Q295I, Q295M, Y296H, Y296W, S298A, S298R, Y300I, Y300V, Y300W, R301A, R301M, R301P, R301S, V302A, V302F, V302L, V302M, V302R, V302S, V303S, V303Y, S304T, V305A, V305F, V305I, V305L, V305R and V305S of said Fc fragment; the numbering being that of the EU index or the Kabat equivalent.
(ii) a mutation selected from 378V, 378T, 434Y and 434S.

In another embodiment, the Fc fragments have at least one mutation selected from:
G316D, K326E, N315D, N361H, P396L, T350A, V284L, V323I, P352S, A378V, Y436H, V266M, N421T, G385R, K326T, H435R, K447N, N434K, K334N, V397M, E283G, A378T, F423L, A431V, F423S, N325S, P343S, K290E, S375R, F405V, K322E, K340E, N389S, F243I, T307P, N389T, S442F, K248E, Y349H, N286I, T359A, S383R, K334R, T394P, V259A, T393A, P352L, Q418P, V302A, L398P, F423P, S442P, V363I, S383N, S254F, K320E, G402D, I253F, V284A, A431T, N315H, Y319H, C226Y, F405L, T393I, N434S, R255W, A287T, N286Y, A231V, K274R, V308G, K414R, M428T, E345G, F243L, P247T, Q362R, S440N, Y278H, D312G, V262A, V305A, K246R, V308I, E380G, N276S, K439Q, S267G, F423Y, A231T, K320R, L410R, K320M, V412M, T307N, T366A, P230S, Y349S, A339T, K246E, K274E, A231P, I336T, S298N, L234P, S267N, V263A, E333G, V308A, K439R, K392R, S440G, V397I, I336V, Y373D, K288E, L309P, P227S, V379A, K288R, K320T, V282A, I377T, N421S and C261R, the numbering being that of the EU index or the Kabat equivalent.

In a particular embodiment, the Fc fragments have at least a combination of 2 mutations, said combination being selected from:
  (i) a mutation selected from 307N, 326E, 326T, 334N, 334R, 352L, 378V, 378T, 394P, 396L, 397M and 421T and;
  (ii) at least one mutation selected from 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A, 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N, the numbering being that of the EU index or the Kabat equivalent and with the condition that mutation (i) is not on the same amino acid as mutation (ii).

Preferably, the mutated Fc fragments have an increased affinity for complement C1q, and comprise at least a combination of 2 mutations, said combination comprising:
  i) a mutation selected from 378V, 378T, 396L, 421T, 334R and 326E; and
  ii) at least one mutation selected from 361H, 290E, 316D, 248E, 410R, 421T, 334R, 394P, 307P, 447N, 378V, 284L, 421T, 396L, 286I, 315D and 397M, the numbering being that of the EU index or the Kabat equivalent and with the condition that mutation (i) is not on the same amino acid as mutation (ii).

Preferably, the mutated Fc fragments have an increased affinity for FcγRIIIa (CD16a), and comprise at least a combination of 2 mutations, said combination comprising:
  i) a mutation selected from 378V, 326E, 397M, 334N and 396L; and
  ii) at least one mutation selected from 316D, 397M, 334N, 248E, 231V, 246R, 336T, 421T, 361H, 366A, 439R, 290E, 394P, 307P, 378V, 378T, 286I, 286Y and 298N, the numbering being that of the EU index or the Kabat equivalent and with the condition that mutation (i) is not on the same amino acid as mutation (ii).

Preferably, the mutated Fc fragments have an increased affinity for FcγRIIa (CD32a), and comprise at least a combination of 2 mutations, said combination comprising:
  i) a mutation selected from 378V, 326E, 397M, 307N, 394P, 326T, 396L and 334N; and
  ii) at least one mutation selected from: 316D, 334R, 334N, 323I, 231V, 246R, 336T, 378T, 286Y, 286I, 352S, 383R, 359A, 421T, 361H, 315D, 366A, 290E, 307P and 439R, the numbering being that of the EU index or the Kabat equivalent and with the condition that mutation (i) is not on the same amino acid as mutation (ii).

Preferably, the mutated Fc fragments have an increased affinity for FcγRIIb (CD32b), and comprise at least a combination of 2 mutations, said combination comprising:
  i) a mutation selected from 326E, 326T, 378V, 397M, 352L, 394P, 396L and 421T; and
  ii) at least one mutation selected from 316D, 334R, 248E, 334N, 418P, 231V, 320E, 402D, 359A, 383R, 421T and 361H, the numbering being that of the EU index or the Kabat equivalent and with the condition that mutation (i) is not on the same amino acid as mutation (ii).

Preferably, the mutated Fc fragments comprise at least a combination of 3 mutations, said combination comprising:
  (i) a mutation selected from 326E, 326T, 352L, 378V, 378T, 396L, 397M, 421T, 334N, 334R, 307N and 394P; and
  (ii) at least 2 mutations selected from 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A, 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N, the numbering being that of the EU index or the Kabat equivalent and with the condition that mutation (i) is not on the same amino acid as mutation (ii).

In a particularly advantageous embodiment, the Fc fragments have a combination of mutations selected from K334N/P352S/V397M/A378V (combination of mutations also called "A3A-184A"; Fc fragments with this combination of mutations are thus also called "A3A-184A"), G316D/K326E/A378V (combination of mutations also called "A3A-105D"; Fc fragments with this combination of mutations are thus also called "A3A-105D"), P396L/N421T/A378V (combination of mutations also called "J3B-118A"; Fc fragments with this combination of mutations are also called "J3B-118A").

The sequence of fragment A3A-184A (K334N/P352S/A378V/V397M) is presented in the sequence listing, as SEQ ID NO: 19:

DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIENTISKAKGQPREPQVYTLSPSRDELTKNQVS

LTCLVKGFYPSDIVVEWESNGQPENNYKTTPPMLDSDGSFFLYSKLTV

DKSRWQQGNVFSCSVMHEALHNHYTQKSLSLSPGK

The sequence of fragment A3A-105D (G316D/K326E/A378V) is presented in the sequence listing, as SEQ ID NO: 20:

DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLND

KEYKCKVSNEALPAPIEKTISKAKGQPREPQVYTLPPSRDELTKNQVS

LTCLVKGFYPSDIVVEWESNGQPENNYKTTPPVLDSDGSFFLYSKLTV

DKSRWQQGNVFSCSVMHEALHNHYTQKSLSLSPGK

The sequence of fragment J3B-118A (A378V/P396L/N421T) is presented in the sequence listing, as SEQ ID NO: 21:

DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVS

LTCLVKGFYPSDIVVEWESNGQPENNYKTTPLVLDSDGSFFLYSKLTV

DKSRWQQGTVFSCSVMHEALHNHYTQKSLSLSPGK

According to another particular embodiment, the mutated Fc fragments used in the invention have a deletion of an amino acid at position 293 or 294 (DEL293 or DEL294), the numbering of the Fc fragment amino acids referring to that of the EU index or the Kabat equivalent. This deletion may be the only mutation of the Fc fragment, or may be accompanied by other mutations, in particular among those listed above.

This single mutation leads to a specific glycosylation of the fragment, namely a hypersialylation, which is particularly advantageous with respect to glycoprotein half-life and to inflammatory processes.

According to another more particular embodiment, the mutated Fc fragments used in the invention have the deletion of the amino acid at position 293 or 294, and have in addition one or more mutations at positions selected from the following list: 226, 230, 241, 256, 259, 264, 307, 315, 330, 342, 361, 362, 378, 382, 383, 389, 396, 397, 421, 428 and 434.

For example, a preferred Fc fragment has the combination of mutations 307P, 434Y, in combination with deletion DEL294 or DEL293.

According to another aspect of the invention, use is made of a composition comprising a plurality of Fc fragments which all have substantially the same sequence, and which, taken as a whole, have a specific glycosylation profile.

According to a particular aspect, a composition used in the context of the invention comprises Fc fragments having N-glycans on the glycosylation site (Asn 297) thereof, characterized in that said N-glycans of the Fc fragments have a degree of fucosylation lower than 65%, preferably lower than 60%, preferably lower than 55%, preferably lower than 50%, more preferably lower than 45%, preferably lower than 40%, preferably lower than 35%, preferably lower than 30%, preferably lower than 25%, preferably lower than 20%.

According to still another aspect, a composition used in the context of the invention comprises Fc fragments, said Fc fragments having N-glycans on the glycosylation site (Asn 297) thereof, characterized in that said N-glycans of the Fc fragments have a biantennary-type glycan structure, with short chains, a low sialylation, with terminal mannoses and/or non-intercalated terminal N-acetylglucosamines.

According to a more particular aspect, a composition used in the context of the invention comprises Fc fragments, said Fc fragments having N-glycans on the glycosylation site (Asn 297) thereof, characterized in that greater than 60% of said N-glycans of the Fc fragments are the G0+G1+G0F+G1F forms, the G0F+G1F forms being less than 50%.

According to another more particular aspect, a composition used in the context of the invention comprises Fc fragments, said Fc fragments having N-glycans on the glycosylation site (Asn 297) thereof, characterized in that greater than 60% of said N-glycans of the Fc fragments are the G0+G1+G0F+G1F forms, the fucose content being lower than 65%.

According to another even more particular aspect, a composition used in the context of the invention comprises Fc fragments, said Fc fragments having N-glycans on the glycosylation site (Asn 297) thereof, characterized in that less than 40% of said N-glycans of the Fc fragments are the G1F+G0F forms.

According to a more particular aspect, a composition used in the context of the invention comprises Fc fragments having N-glycans on the glycosylation site (Asn 297) thereof, said N-glycans of the Fc fragments having a degree of fucosylation equal to 0%. The invention thus provides a composition comprising Fc fragments having N-glycans on the glycosylation site Asn297 thereof, characterized in that said N-glycans of the Fc fragments are fucose-free.

Also, according to a particular aspect, a composition used in the context of the invention comprises Fc fragments having N-glycans on the glycosylation site Asn297 thereof, characterized in that said N-glycans of the Fc fragments have a degree of fucosylation in the range between 20% and 55%. In particular, the invention provides a composition comprising Fc fragments having N-glycans on the glycosylation site Asn297 thereof, characterized in that said N-glycans of the Fc fragments have a degree of fucosylation in the range between 20% and 50%, between 25% and 55%, between 25% and 50%, between 20% and 45%, or between 25% and 45%.

According to a more particular aspect, a useful composition according to the invention comprises Fc fragments having N-glycans on the glycosylation site Asn297 thereof, characterized in that greater than 60%, preferably greater than 80%, of said N-glycans of the Fc fragments are the G0+G1+G0F+G1F forms, the G0F+G1F forms being less than 50%, preferably less than 40%, or 30%.

According to another more particular aspect, greater than 60% of the N-glycans of the Fc fragments within the composition are the G0+G1+G0F+G1F forms, the fucose content being lower than 65%.

According to still another more particular aspect, less than 50%, preferably less than 40%, or 30% of the N-glycans of the Fc fragments within the composition are the G1F+G0F forms.

Figure 3:
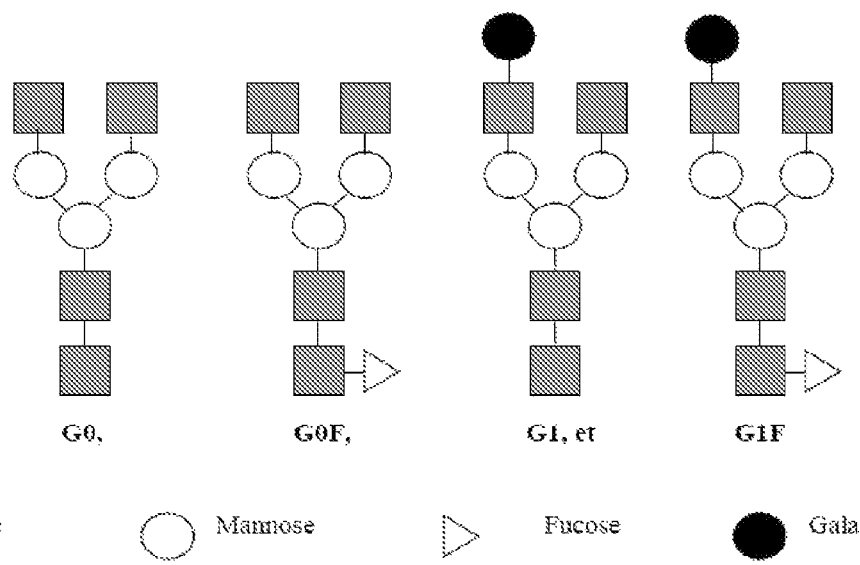
FIG. 3 shows the G0, G0F, G1 and G1F forms of the glycan structures capable of being present on the Fc fragments of the invention.

The G0, G0F, G1 and G1F forms are selected from the forms indicated in FIG. 3.

Advantageously, the N-glycans of the Fc fragments within the composition have an average sialic acid content of less than 25%, 20%, 15% or 10%, preferably 5%, 4%, 3% or 2%.

A composition that may be used in the context of the invention comprises Fc fragments having N-glycans on the glycosylation site (Asn 297) thereof, said N-glycans of the Fc fragments having a biantennary-type glycan structure, with short chains, a low sialylation, with terminal mannoses and/or non-intercalated terminal N-acetylglucosamines, greater than 60% of the N-glycans consisting of the G0+G1+G0F+G1F forms, and a low fucosylation, less than 50% of the N-glycans consisting of the G0F+G1F forms, for example.

In a particular embodiment, the Fc fragments according to the invention have glycan structures as described in patent application WO01/77181.

According to an advantageous embodiment, the Fc fragments used in the invention comprise at least one mutation of an amino acid in comparison with a parent Fc fragment and have N-glycans on the glycosylation site (Asn 297) thereof, said N-glycans of the Fc fragments having a degree of fucosylation lower than 65%, preferably lower than 60%, preferably lower than 55%, preferably lower than 50%, more preferably lower than 45%, preferably lower than 40%, preferably lower than 35%, preferably lower than 30%, preferably lower than 25%, preferably lower than 20%. Preferably, the Fc fragments have one or more mutations at positions selected from those listed above, notably at positions selected from the following list: 226, 230, 241, 256, 259, 264, 307, 315, 330, 342, 361, 362, 378, 382, 383, 389, 396, 397, 421, 428 and 434; and, in addition, on the glycosylation site (Asn 297) thereof, have N-glycans with a degree of fucosylation lower than 55%, preferably lower than 50%, more preferably lower than 45%, preferably lower than 40%, preferably lower than 35%, preferably lower than 30%, preferably lower than 25%, preferably lower than 20%.

More preferably, the Fc fragments of the composition according to the invention have a combination of mutations selected from 315D/330V/361D/378V/434Y, 230S/315D/428L/434Y, 307A/315D/330V/382V/389T/434Y, 259I/315D/434Y, 256N/378V/383N/434Y and DEL294/307P/434Y; and, in addition, on the glycosylation site (Asn 297) thereof, have N-glycans with a degree of fucosylation lower than 55%, preferably lower than 50%, more preferably lower than 45%, preferably lower than 40%, preferably lower than 35%, preferably lower than 30%, preferably lower than 25%, preferably lower than 20%.

Advantageously, the Fc fragments having a modified glycosylation at the glycosylation site at position 297, in particular a low fucosylation, have an increased binding to Fc-gamma receptors (FcγR), in particular FcγRIIIa (CD16a).

Preferably, said Fc fragments have an affinity for CD16a at least equal to $2 \times 10^6$ $M^{-1}$, at least equal to $2 \times 10^7$ $M^{-1}$, $2 \times 10^8$ $M^{-1}$ or $2 \times 10^9$ $M^{-1}$, as determined by Scatchard analysis or BIAcore technology (label-free surface plasmon resonance-based technology).

Particularly advantageously, the mutated Fc fragments of the invention may be used in combination with different mutated Fc fragments having different mutations. For example, use may advantageously be made of a mixture of mutated Fc Fc-Del294, mutated Fc T5A-74 (to also target FcRn), mutated Fc improved for binding to FcγRs (types A3A-184A).

Production of the Fc Fragments According to the Invention

The Fc fragments used in the invention may be produced by any method known to persons skilled in the art, for example by chemical synthesis or by recombination.

In a preferred embodiment, the Fc fragments used in the invention are referred to as "recombinant," i.e., they are obtained by recombination.

When the Fc fragments according to the invention have a mutation of one or more amino acids, the mutation(s) may optionally be introduced by known techniques such as gene synthesis, directed mutagenesis, notably obtained by PCR with specific primers that introduce the desired mutations, or random mutagenesis. Preferably, random mutagenesis as described in application WO02/038756 is used, namely the MutaGen technique. This technique uses a human DNA mutase, notably selected from DNA polymerases β, η and ι. Conventional recombinant techniques involve recombination in a host cell, transformed with one or more vectors that enable expression with or without secretion of the Fc fragment sequence into the extracellular medium. The vector generally comprises a promoter, signals for initiation and termination of translation, as well as appropriate regions for regulation of transcription. It may be maintained stably in the host cell and may optionally have particular signals that specify secretion of the translated protein. These various elements are selected and optimized by persons skilled in the art according to the host cell used.

Such vectors are prepared by methods commonly used by persons skilled in the art, and the resulting clones may be introduced into a suitable host by standard methods, such as lipofection, electroporation, use of polycationic agents, heat shock, or chemical methods.

The host cell may be selected from prokaryotic or eukaryotic systems, for example bacterial cells but also yeast cells or animal cells, in particular mammalian cells. Insect cells or plant cells may also be used.

The Fc fragments used in the invention may be produced by culturing, in suitable medium and culture conditions, a host cell expressing said Fc fragments; and recovering the fragments thus produced from the culture medium or from said cultured cells.

The preferred mammalian cells for expressing the Fc fragments are the rat cell line YB2/0, the cell line Vero, the hamster cell line CHO, in particular the cell lines CHO dhfr– and CHO Lec13, CHO-lec10, CHO-lec1, CHOK1SV Potelligent® (Lonza, Switzerland), CHOGnTIII (Glycart, Switzerland), PER.C6™ (Crucell), HEK293, T1080, EB66, K562, NS0, SP2/0, BHK or COS.

Another production mode is expression of the Fc fragments in transgenic organisms, for example in plants (Ayala M, Gavilondo J, Rodríguez M, Fuentes A, Enríquez G, Perez L, Cremata J, Pujol M. Production of plantibodies in *Nicotiana* plants. Methods Mol Biol. 2009; 483:103-34.) or in the milk of transgenic animals such as rabbits, goats, rats or pigs (Pollock, D. P., J. P. Kutzko, E. Birck-Wilson, J. L. Williams, Y. Echelard and H. M. Meade. (1999). Transgenic milk as a method for the production of recombinant antibodies. Journal of Immunological Methods. 231:147-157). Also see document WO200748077 in this respect.

In an alternative embodiment, the Fc fragments are obtained by proteolytic treatment of immunoglobulins that are themselves mutated.

The glycosylation of the Fc fragments may be modified by known techniques. The Fc fragments having glycosylation according to the invention may notably be produced from the cleavage of the antibodies produced according to the technique described in WO01/77181, notably by the enzyme papain. Slightly fucosylated Fc fragments may also be obtained by production in cells cultured in the presence of kifunensine, as described for example in document U.S. Pat. No. 7,700,321, or in cells for which the GDP-fucose production pathway is inhibited, for example by inhibition of at least one enzyme of the fucose production cycle (see notably documents US 2010291628 or US 20090228994, EP 1500698, EP 1792987 or U.S. Pat. No. 7,846,725). It is also possible to use interfering RNA (RNAi) that inhibit 1,6-fucosyltransferase as described in document U.S. Pat.

No. 7,393,683 or document WO2006133148. It may be a matter of preparation methods in yeasts, as described for example in document WO 0200879.

If the Fc fragments have 100% non-fucosylated oligosaccharides, i.e., when the Fc fragments are completely fucose-free, it is possible to use preparation methods known to persons skilled in the art, such as for example those disclosed in documents EP1176195, U.S. Pat. Nos. 7,214,775, 6,994,292, 7,425,449, US2010223686, WO2007099988, EP 1705251, this list being non-limiting. It may be a matter for example of a method using a host cell expressing at least one nucleic acid encoding an Fc fragment, and of which the glycosylation is modified by deletion of the gene encoding α1,6-fucosyltransferase or by addition of a mutation of said gene to eliminate α1,6-fucosyltransferase activity, and consequently expressing a fucose-free antibody fragment.

Therapeutic Applications

Because of their many advantages, in terms of both efficacy and optimized effector functions or reduced side effects, the Fc fragments described herein are useful in the treatment of an autoimmune and/or inflammatory disease.

A method is described herein for treating an autoimmune and/or inflammatory disease in a patient, comprising administering to said patient a therapeutically effective amount of Fc fragments with an altered affinity for at least one Fc receptor as described herein.

In the present invention, the expression "an autoimmune and/or inflammatory disease" refers to an organ-specific or systemic, primary or secondary autoimmune and/or inflammatory disease, optionally associated with pathogenic autoantibodies.

For example, the disease may be selected from thrombocytopenic thrombotic purpura (TTP), idiopathic thrombotic purpura (ITP), organ or graft rejection, graft-versus-host disease, rheumatoid arthritis, systemic lupus erythematosus, the different types of sclerosis, primary Sjögren syndrome (or Gougerot-Sjögren syndrome), autoimmune polyneuropathies such as multiple sclerosis, type 1 diabetes, autoimmune hepatitis, ankylosing spondylitis, Reiter syndrome, gouty arthritis, celiac disease, Crohn's disease, Hashimoto's thyroiditis (hypothyroidism), Addison disease, autoimmune hepatitis, Basedow disease (hyperthyroidism), ulcerative colitis, vasculitis such as antineutrophil cytoplasmic antibody (ANCA)-associated systemic vasculitis, autoimmune cytopenias and other hematological complications in adults and children, such as acute or chronic autoimmune thrombopenia, autoimmune hemolytic anemia, hemolytic disease of the newborn (HDN), cold agglutinin disease, thrombocytopenic thrombotic purpura and acquired autoimmune hemophilia; Goodpasture syndrome, extra-membranous nephropathy, autoimmune bullous skin disorders, refractory myasthenia, mixed cryoglobulinemia, psoriasis, juvenile chronic arthritis, inflammatory myositis, dermatomyositis and systemic autoimmune disease in children including antiphospholipid syndrome, connective tissue disease, the different types of sclerosis, pulmonary autoimmune inflammation, Guillain-Barré syndrome, Kawasaki disease, multifocal motor neuropathy (MMN), chronic demyelinating inflammatory polyradiculoneuropathy (CDIP), autoimmune thyroiditis, mellitus, myasthenia gravis, inflammatory autoimmune disease of the eye, neuromyelitis optica (Devic disease), scleroderma, pemphigus, diabetes due to insulin resistance, polymyositis, Biermer anemia, glomerulonephritis, Wegener disease, giant cell arteritis, periarteritis nodosa and Churg-Strauss syndrome, Still's disease, atrophic polychondritis, Behçet's disease, monoclonal gammopathy, Wegener's granulomatosis, lupus, ulcerative colitis, psoriatic rheumatism, sarcoidosis, collagenous colitis, dermatitis herpetiformis, familial Mediterranean fever, glomerulonephritis with deposits of IgA, Lambert-Eaton myasthenic syndrome, sympathetic ophthalmia, Fiessinger-Leroy-Reiter syndrome and uveomeningoencephalitic syndrome.

Other inflammatory diseases are also included, such as for example acute respiratory distress syndrome (ARDS), acute septic arthritis, adjuvant arthritis, allergic encephalomyelitis, allergic rhinitis, allergic vasculitis, allergy, asthma, atherosclerosis, chronic inflammation due to chronic bacterial or viral infections, chronic obstructive pulmonary disease (COPD), coronary heart disease, encephalitis, inflammatory bowel disease, inflammatory osteolysis, inflammation associated with acute and delayed hypersensitivity reactions, inflammation associated with tumors, peripheral nerve damage or demyelinating diseases, inflammation associated with tissue trauma such as burns and ischemia, inflammation due to meningitis, multiple organ dysfunction syndrome (MODS), pulmonary fibrosis, septicemia and septic shock, Stevens-Johnson syndrome, undifferentiated arthritis, and undifferentiated spondyloarthropathy.

In a particular embodiment of the invention, the autoimmune disease is idiopathic thrombotic purpura (ITP) and chronic demyelinating inflammatory polyradiculoneuropathy (CDIP).

One of the effects observed is notably a limitation or a reduction of the destruction of platelets observed in ITP pathology and a limitation or a reduction of the loss of the myelin sheath of peripheral nerves in CDIP.

In another particular embodiment, the disease is an inflammatory disease, such as in particular graft-versus-host disease. In this case, Fc fragments with a mutation that induces hypersialylation, such as a deletion of an amino acid at position 294 (DEL294) or 293 (DEL293), are particularly advantageous.

Any route of administration is envisaged, notably parenteral routes, such as the intravenous, intramuscular, subcutaneous, intradermal or topical routes, or via the mucosal route, for example by inhalation. The enteral (oral, rectal) and intrathecal routes are also possible. Preferably, the intravenous route is used.

The Fc fragments according to the invention are generally formulated within pharmaceutical compositions comprising pharmaceutically acceptable excipients.

The pharmaceutical compositions may be in any pharmaceutical form suited to the selected route of administration.

The useful pharmaceutical compositions according to the invention advantageously comprise one or more pharmaceutically acceptable excipients or carriers. For example, mention may be made of saline, physiological, isotonic or buffered solutions, etc., compatible with pharmaceutical use and known to persons skilled in the art. The compositions may contain one or more agents or carriers selected from dispersants, solubilizers, stabilizers, preservatives, etc. Agents or carriers usable in formulations (liquid and/or injectable and/or solid) are notably methylcellulose, hydroxymethylcellulose, carboxymethylcellulose, polysorbate 80, mannitol, gelatin, lactose, plant oils, acacia, etc. The compositions may optionally be formulated by means of pharmaceutical forms or devices providing extended and/or delayed release. For this type of formulation, an agent such as cellulose, carbonate or starch is advantageously used.

The administered doses may vary, inter alia, according to the patient's weight and age, and the severity of the disease, assessed by the person skilled in the art.

In a preferred embodiment, the dosage of the Fc fragments according to the invention is in the range from about 0.05 mg/kg to about 1 g/kg of body weight, i.e., about 20 mg to about 100 g per day for an adult. Preferably, the dosage is from about 330 mg/kg to about 660 mg/kg per day.

The following examples illustrate the invention without limiting the scope thereof.

Construction of Expression Vectors for the Recombinant Fc (WT and Mutated):

The sequence of the recombinant Fc (aa 221-447) was cloned into a generic eukaryotic expression vector derived from pCEP4 (Invitrogen) for expression in HEK cells and into the OptiCHO vector for expression in YB2/0 cells using standard PCR protocols.

All the mutations of interest in the Fc fragment were inserted into the expression vector by overlapping PCR using two primers containing the mutation. The fragments thus obtained by PCR were then combined and the resulting fragment was amplified by PCR using standard protocols. The PCR product was purified on 1% (w/v) agarose gel, digested with adequate restriction enzymes and cloned into the expression vector for the recombinant Fc.

Figure 7:
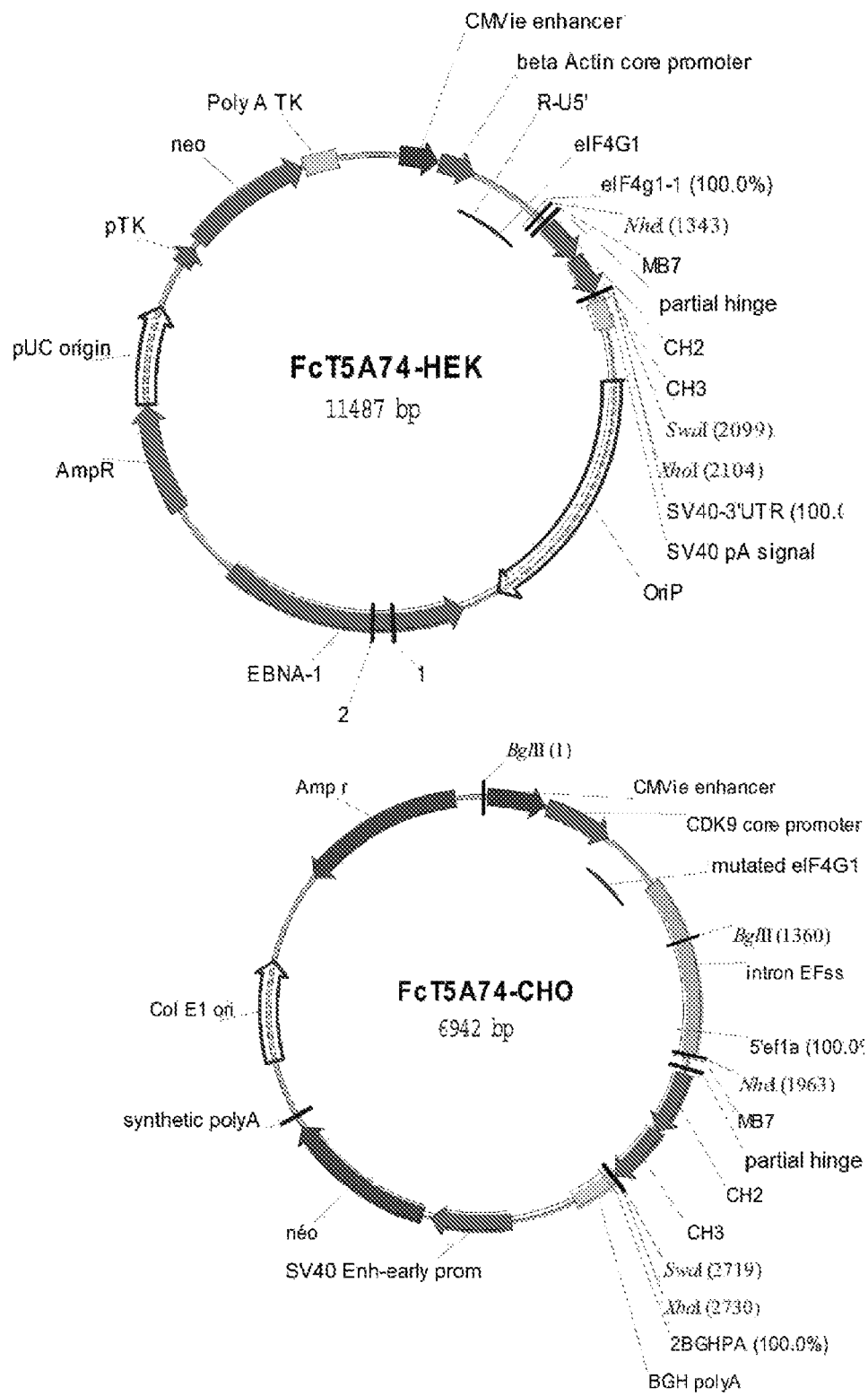
FIG. 7 shows the map of the pCEP4 vector used for expression of variant T5A-74, defined below, and the map of the OptiCHO vector used for expression of variant T5A-74.

FIG. 7 shows the map of the pCEP4 vector used for expression of variant T5A-74 in HEK cells, and the map of the OptiCHO vector used for expression of variant T5A-74 in YB2/0 cells.

Production of the Recombinant Fc in HEK Cells

HEK 293 cells were transfected with the pCEP4 expression vector for the recombinant Fc (WT or mutated) according to standard protocols (Invitrogen). The cells were cultured so as to produce antibodies transiently. The antibodies produced were able to be isolated and purified according to standard techniques of the art, with a view to the characterization thereof. The production rates obtained are on the order of 150 to 500 µg/mL. The purity and the quality of the products were verified by SDS-PAGE and SEC.

Production of Recombinant Fc in YB2/0 Cells

YB2/0 cells were stably transfected by electroporation with the OptiCHO expression vector for the recombinant Fc (WT or mutated) according to standard protocols. Production was carried out in stable pools or after cloning of YB2/0 cells.

The steps of producing the antibodies by cell culture and of purifying same were carried out according to standard techniques of the art, with a view to the characterization thereof. The production rates obtained are on the order of 3 to 30 µg/mL. The purity and the quality of the products were verified by SDS-PAGE and SEC.

Example 1: Efficacy Test (Inhibition of Red Blood Cell Lysis)

To mimic the situation of red blood cell lysis observed in idiopathic thrombocytopenic purpura (ITP), involving the ITP patient's autoantibodies, effector-cell mediated red blood cell lysis in the presence of a monoclonal anti-Rhesus D (RhD) antibody was carried out, and the capacity of various amounts of polyvalent immunoglobulins (IVIg) or of recombinant Fc fragments, mutated (recombinant Fc fragments containing the mutations according to Table 1 below) and non-mutated, to inhibit said lysis, for example by competition with anti-RhD for Fc receptor binding to the surface of effector cells, was evaluated.

TABLE 1

Constructions of preferred mutated Fc variants of the invention
The table below represents the different variants of mutated Fc fragments tested in the experiments for the efficacy test (inhibition of red blood cell lysis) and for the test of binding to human FcRn and CD16aV by surface plasmon resonance (SPR).

| Name | Variant | Mutation(s) added |
|---|---|---|
| T5A-74I | T5A-74 | T260A |
| T5A-74J | T5A-74 | E258I |
| T5A-74K | T5A-74 | K290Y |
| T5A-74L | T5A-74 | E294A |
| T5A-74M | T5A-74 | Y296W |
| ZAC2-85 | WT | T260A |
| ZAC3-172 | WT | K290Y |
| A3A-184A | WT | K334N, P352S, V397M, A378V |
| A3A-105D | WT | G316D, K326E, A378V |
| J3B-118A | WT | P396L, N421T, A378V |

To that end, as effector cells, peripheral blood mononuclear cells (PBMC) were purified from peripheral blood by Ficoll gradient. Rh-D+ red blood cells obtained from healthy Rh-D+ blood donors were mixed with an anti-RhD monoclonal antibody. The PBMC were incubated with opsonized Rh-D+ red blood cells (effector/target ratio of 2:1).

Figure 4:
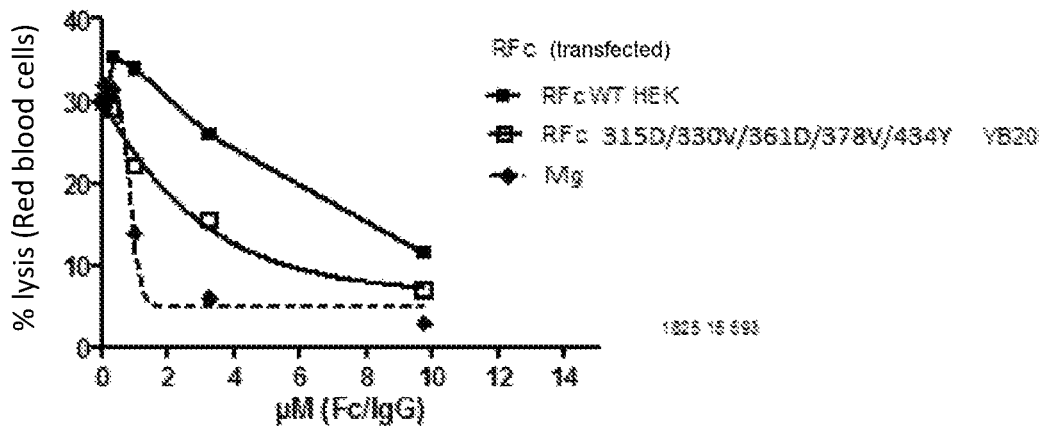
FIG. 4 is a graph presenting the percent of effector cell-mediated lysis of Rhesus D+ red blood cells in the presence of a monoclonal anti-Rhesus D (RhD) antibody, observed following the addition of various amounts of polyvalent immunoglobulins (IVIg) or recombinant Fc fragments, non-mutated or mutated (Fc fragment containing the mutations 315D/330V/361D/378V/434Y).
Figure 5:
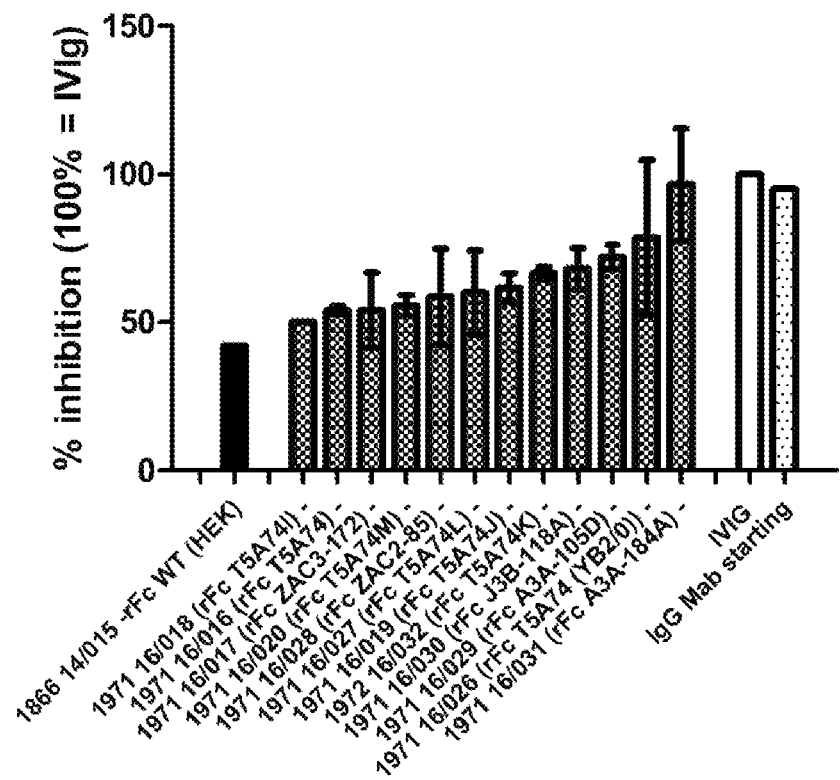
FIG. 5 is a graph presenting the percent of effector cell-mediated lysis of Rhesus D+ red blood cells in the presence of a monoclonal anti-Rhesus D (RhD) antibody, observed following the addition of various amounts of polyvalent immunoglobulins (IVIg) or recombinant Fc fragments, non-mutated or mutated (Fc fragment containing the mutations according to Table 1). "rFc WT" denotes the wild-type recombinant Fc fragment. The positive controls are represented by: IVIG (i.e., mixture of plasma antibodies extracted from human plasma—IVIGs are the reference treatment for idiopathic thrombocytopenic purpura (ITP)); and "IgG Mabs starting", which corresponds to the Herceptin Fc fragment (antibody produced transgenically in a mammal and then subjected to papain digestion to generate the Fc fragment).

To evaluate the capacity of the candidates (IVIg and recombinant Fc fragments, mutated as defined according to Table 1 and non-mutated) to inhibit cytotoxicity induced by an anti-RhD antibody by competition and/or saturation of Fc receptors, various concentrations of the candidates (0 to 9.75 µM) were added to each well. After 16 hours, the percentage of lysed red blood cells was estimated chromogenically by measuring the amount of hemoglobin released into the supernatants (measurement of optical density (OD)). Specific lysis is calculated in percentage according to the following formula:

OD sample−OD control 0%/OD control 100%−OD control 0%×100=% Lysis wherein:
"OD control 100%" corresponds to total lysis of red corpuscles (for example $NH_4Cl$)
"OD control 0%" corresponds to the lysis observed with a reaction mixture without antibody
The results are expressed as % specific lysis (see FIGS. 4 and 5).

Example 2: Test of Binding to Human FcRn and CD16aV by Surface Plasmon Resonance (SPR) on Biacore X100

Proteins Used:

Recombinant human FcRn (FcRn α and β2-microglobulin) was produced in baculovirus cells by GTP Technology (Labege, France) as previously described (Popov et al., Mol. Immunol. 33:521-530 (1996)). Recombinant human CD16aV is available commercially (R&D Systems).

Test on FcRn:

The FC1 and FC2 cells of a CM5 chip (Biacore, GE Healthcare) were activated for 3 minutes with a 1:1 mixture of 0.1 M N-hydroxysuccinimide and 0.1 M 3-(N,N-dimethylamino)propyl-N-ethylcarbodiimide at 30 µL/min. Recombinant FcRn was then immobilized on the FC2 cell at 32.6 µg/mL in 10 mM sodium acetate buffer (pH 5) (immobilization for 100 seconds, final immobilization level of 350 RU). The FC1 cell was used as negative control, prepared in the same manner as FC2 but in the absence of recombinant FcRn. The recombinant Fc to be tested were injected at 6 different concentrations (300 nM, 150 nM, 75 nM, 30 nM, 15 nM and 0) in 50 mM Na phosphate, 150 mM NaCl, 0.05% Tween 20 buffer (pH 6) for 8 minutes at 10 µL/min on the FC1 and FC2 cells. The FC1 and FC2 cells were regenerated between each sample concentration by an injection for 1 minute of 50 mM Na phosphate, 150 mM NaCl, 0.05% Tween 20 buffer (pH 7.8). The data generated were analyzed with the BIAevaluation version 3.1 software (Biacore), by subtracting the control signal obtained on FC1 from the test signal obtained on FC2.

Test on CD16aV:

The FC1 and FC2 cells of a CM5 chip (Biacore, GE Healthcare) were prepared with the His Capture Kit (GE Healthcare, item 28-9950-56), so as to immobilize the anti-histidine antibody at 50 µg/mL (flow rate of 5 µL/min, EDC/NHS activation for 7 minutes, immobilization for 7 minutes, final immobilization level of 12,000 RU on FC1 and FC2). Recombinant human CD16aV was immobilized on the FC2 cell (1 µg/mL in HBS-EP+, Biacore, GE Healthcare) for 60 seconds at 5 µL/min. The recombinant Fc to be tested were injected on the FC1 and FC2 cells at 5 different concentrations (1000 nM, 500 nM, 250 nM, 125 nM and 25 nM) in HBS-EP+ buffer in single cycle kinetics (SCK) conditions, with a contact time of 60 seconds, a dissociation of 300 seconds and a flow rate of 30 µL/min without regeneration between each concentration. The final regeneration, between each recombinant Fc, was carried out in 10 mM glycine buffer (pH 1.5) for 60 seconds at 30 µL/min on the FC1 and FC2 cells. The data generated were analyzed with the BIAevaluation version 3.1 software (Biacore), by subtracting the control signal obtained on FC1 from the test signal obtained on FC2.

The invention claimed is:

1. A method for treating an autoimmune disease in a subject, the method comprising administering an antibody Fc fragment composition to the subject, wherein said antibody Fc fragment composition comprises isolated Fc fragments having an improved affinity for FcγRIII receptor (CD16a) by a ratio of at least 2 as compared to a parent Fc fragment, and wherein the Fc fragments comprise a combination of mutations K334N/P352S/A378V/V397M in comparison with the parent Fc fragment, wherein the parent Fc fragment is the Fc fragment of wild-type IgG1 of SEQ ID NO:6, wherein the numbering of the Fc fragment amino acids refers to that of the EU index or the Kabat equivalent, and wherein the autoimmune disease is selected from the group consisting of idiopathic thrombotic purpura, chronic demyelinating inflammatory polyradiculoneuropathy (CDIP), and myasthenia gravis.

2. The method according to claim 1, wherein the isolated Fc fragments consist in SEQ ID NO: 19.

3. The method of claim 1, wherein the Fc fragments are obtained recombinantly.

4. The method of claim 1, wherein the Fc fragments have N-glycans on the glycosylation site (Asn 297) thereof, and wherein the Fc fragments of the Fc fragment composition have a degree of fucosylation that is less than 65%.

5. The method of claim 1, wherein the Fc fragments have N-glycans on the glycosylation site (Asn 297) thereof, and said N-glycans of the Fc fragments have a biantennary-type glycan structure comprising terminal mannoses and/or non-intercalated terminal N-acetylglucosamines.

6. The method of claim 1, wherein the Fc fragments have N-glycans on the glycosylation site (Asn 297) thereof, and greater than 60% of said N-glycans of the Fc fragments are the G0+G1+G0F+G1F forms, the G0F+G1F forms being less than 50%.

7. The method of claim 1, wherein the Fc fragments have N-glycans on the glycosylation site (Asn 297) thereof, and greater than 60% of said N-glycans of the Fc fragments are the G0+G1+G0F+G1F forms, the fucose content being lower than 65%.

8. The method of claim 1, wherein the Fc fragments have N-glycans on the glycosylation site (Asn 297) thereof, and less than 40% of the N-glycans in the Fc fragment composition are the G1F+G0F forms.

* * * * *